(12) United States Patent
Dixon et al.

(10) Patent No.: US 9,309,528 B2
(45) Date of Patent: Apr. 12, 2016

(54) BIOFUEL PRODUCTION METHODS AND COMPOSITIONS

(75) Inventors: Richard A. Dixon, Ardmore, OK (US); Fang Chen, Ardmore, OK (US); Zengyu Wang, Ardmore, OK (US)

(73) Assignee: The Samuel Roberts Noble Foundation, Inc., Ardmore, OK (US)

( * ) Notice: Subject to any disclaimer, the term of this patent is extended or adjusted under 35 U.S.C. 154(b) by 1280 days.

(21) Appl. No.: 11/944,217

(22) Filed: Nov. 21, 2007

(65) Prior Publication Data

US 2008/0274528 A1    Nov. 6, 2008

Related U.S. Application Data

(60) Provisional application No. 60/866,764, filed on Nov. 21, 2006.

(51) Int. Cl.
  *A01H 5/00*     (2006.01)
  *A01H 5/10*     (2006.01)
  *C12N 15/82*    (2006.01)
  *C12P 7/06*     (2006.01)

(52) U.S. Cl.
  CPC ........ *C12N 15/8245* (2013.01); *C12N 15/8255* (2013.01); *Y02E 50/17* (2013.01)

(58) Field of Classification Search
  None
  See application file for complete search history.

(56) References Cited

U.S. PATENT DOCUMENTS

| | | | |
|---|---|---|---|
| 3,990,944 A | 11/1976 | Gauss et al. | 195/33 |
| 4,461,648 A | 7/1984 | Foody | 127/37 |
| 4,600,590 A | 7/1986 | Dale | 426/69 |
| 5,037,663 A | 8/1991 | Dale | 426/69 |
| 5,451,514 A | 9/1995 | Boudet et al. | 435/172.3 |
| 5,705,369 A | 1/1998 | Torget et al. | 195/33 |
| 5,817,381 A | 10/1998 | Chen et al. | 428/34.8 |
| 5,850,020 A | 12/1998 | Bloksberg et al. | 800/205 |
| 5,922,928 A | 7/1999 | Chiang et al. | 800/205 |
| 5,981,837 A | 11/1999 | Chapple | 800/278 |
| 6,090,595 A | 7/2000 | Foody et al. | 435/99 |
| 6,204,434 B1 | 3/2001 | Bloksberg et al. | 800/290 |
| 6,419,788 B1 | 7/2002 | Wingerson | 162/14 |
| 6,555,350 B2 | 4/2003 | Ahring et al. | 435/162 |
| 6,610,908 B1 | 8/2003 | Chapple | 800/287 |
| 6,620,292 B2 | 9/2003 | Wingerson | 162/19 |
| 6,653,528 B1 | 11/2003 | Bloksberg et al. | 800/278 |
| 6,660,506 B2 | 12/2003 | Nguyen et al. | 435/165 |
| 6,768,042 B2 | 7/2004 | Yanofsky et al. | 800/290 |
| 6,841,721 B2 | 1/2005 | Yanofsky et al. | 800/290 |
| 6,846,677 B2 | 1/2005 | Yanofsky et al. | 435/468 |
| 6,855,180 B1 | 2/2005 | Pinatti et al. | 44/307 |
| 6,855,864 B2 | 2/2005 | Chiang et al. | 800/278 |
| 6,906,240 B2 | 6/2005 | Yanofsky et al. | 800/285 |
| 7,049,485 B2 | 5/2006 | Sticklen et al. | 800/288 |
| 8,362,322 B2 * | 1/2013 | Apuya et al. | 800/284 |
| 2003/0005481 A1 | 1/2003 | Yanofsky et al. | 800/278 |
| 2003/0070779 A1 | 4/2003 | Bransby | 162/97 |
| 2003/0131373 A1 * | 7/2003 | Bloksberg et al. | 800/278 |
| 2004/0034888 A1 * | 2/2004 | Liu et al. | 800/289 |
| 2004/0049802 A1 * | 3/2004 | Dixon et al. | 800/278 |
| 2004/0185542 A1 | 9/2004 | Yang et al. | 435/161 |
| 2005/0050585 A1 | 3/2005 | Chiang et al. | 800/278 |
| 2005/0150008 A1 | 7/2005 | Demmer et al. | 800/284 |
| 2005/0166283 A1 * | 7/2005 | Chiang et al. | 800/278 |
| 2006/0088922 A1 | 4/2006 | Yang et al. | 435/161 |
| 2006/0260011 A1 * | 11/2006 | Carter et al. | 800/285 |

FOREIGN PATENT DOCUMENTS

| | | |
|---|---|---|
| WO | WO 2005/024037 | 3/2005 |
| WO | WO 2006/007557 | 1/2006 |
| WO | WO 2006/012594 | 2/2006 |

OTHER PUBLICATIONS

Reddy et al 2005 PNAS, 102:16573-16578, provided by Applicant.*
Vogel, 2001, Crit. Rev. Plant Sci., 20:15-49.*
Mosier et al, 2005, Bioresource Tech., 96:673-686.*
"2006 Awards," Plant Feedstocks Genomics for Bioenergy, U.S. Department of Energy Office of Science, genomics.energy.gov., Press Release, Aug. 9, 2006.
"Foundation wins grant for research," *The Oklahoman*, Nov. 22, 2005.
"USDA awards $12.6 million for biomass research and development," *State News Service*, Oct. 6, 2005.
Anderson et al., Development of Biotechnological Resources for Biofuels—Project Proposal, U.S. Department of Agriculture, cris.csrees.usda.gov/cgi-bin/starfinder/22651/crisassist.txt, undated.
Badger, "Ethanol from cellulose: a general review," In: Trends in New Crops and New Uses, Janick et al. Eds., ASHS Press, Alexandria, VA, 2002.
Baucher et al., "Lignin: genetic engineering and impact on pulping," *Crit. Rev. Biochem Mol. Biol.*, 38(4):305-350, 2003.
Buxon et al., "Lignin constituents and cell-wall digestibility of grass and legume stems," *Crop Sci.*, 28:553-558, 1988.
Carpita, "Structure and biogenesis of the cell walls of grasses," *Annu. Rev. Plant Physiol. Plant Mol. Biol.*, 47-445-476, 1996.
Casler, "In vitro digestibility of dry matter and cell wall constituents of smooth bromegrass forage," *Crop Sci.*, 27:931-934, 1987.
Chen et al., "Biotechnology in trees: towards improved paper pulping by lignin engineering," *Euphytica*, 118:185-195, 2001.
Chen et al., "Multi-site genetic modulation of monolignol biosynthesis suggests new routes for formation of syringyl lignin and wall-bound ferulic acid in alfalfa(*Medicago sativa* L.)," *The Plant Journal*, 48(1):113-124, 2006.

(Continued)

*Primary Examiner* — Shubo (Joe) Zhou
*Assistant Examiner* — Jason Deveau Rosen
(74) *Attorney, Agent, or Firm* — Dentons US LLP

(57) ABSTRACT

The invention provides methods for increasing the level of fermentable carbohydrates in a biofuel crop plant such as alfalfa or switchgrass, by modification of the lignin biosynthetic pathway. Also provided are plants prepared by the methods of the invention. Methods for processing plant tissue and for producing ethanol by utilizing such plants are also provided.

25 Claims, 10 Drawing Sheets

(56) References Cited

OTHER PUBLICATIONS

Comis, "Scientists study feasibility of switchgrass for energy production," U.S. Department of Agriculture, Mar. 10, 2006.
Davison et al., "Variation of S/G ratio and lignin content in a populus family influences the release of xylose by dilute acid hydrolysis," In: Applied Biochemistry and Biotechnology, Humana Press, pp. 427-435, 2006.
Delmer et al., "Cellulose biosynthesis," *The Plant Cell*, 7:987-1000, 1995.
Delmer, "Cellulose biosynthesis: exciting times for a difficult field of study," *Annu. Rev. Plant Physiol. Plant Mol. Biol.*, 50:245-276, 1999.
Dixon et al., "Metabolic engineering: prospects for crop improvement through the genetic manipulation of phenylpropanoid biosynthesis and defense responses—a review," *Gene* 179:6171, 1996.
Dixon et al., "Systematic modification of monolignol pathway gene expression for improved lignocellulose utilization," Plant Feedstocks Genomics for Bioenergy, U.S. Department of Energy Office of Science, genomics.energy.gov., undated.
Duff et al., "Bioconversion of forest products industry waste cellulosics to fuel ethanol: a review," *Bioresource Technology*, 55(1):1-33, 1996.
Esteghlalian et al., "Modeling and optimization of the dilute-sulfuric-acid pretreatment of corn stover, poplar and switchgrass," *Bioresource Technology*, 59:129-136, 1997.
GenBank Database Accession No. AF153824, Jul. 1, 2001.
Gong et al., "Ethanol production from renewable resources," *Advances in Biochemical Engineering/Biotechnology*, 65:207-241, 1999.
Grabber et al., "Digestion kinetics of parenchyma and sclerenchyma cell walls isolated from orchardgrass and switchgrass," *Crop Sci.*, 32:806-810, 1992.
Grabber et al., "Genetic and molecular basis of grass cell-wall degradability. I. Lignin-cell wall matrix interactions," *C.R. Biologies*, 327:455-465, 2004.
Grabber et al., "p-hydroxyphenyl, guaiacyl, and syringyl lignins have similar inhibitory effects on wall degradability," *J. Agric. Food Chem.*, 45:2530-2532, 1997.
Guo et al., "Improvement of in-rumen digestibility of alfalfa forage by genetic manipulation of lignin O-methyltransferases," *Transgenic Res.*, 10:457-464, 2001.
Hamelinck et al., "Ethanol from lignocellulosic biomass: techno-economic performance in short-, middle- and long-term," *Biomass & Bioenergy*, 28:384-410, 2005.
Hoffmann et al., "Silencing of hydroxycinnanioyl-coenzyme a shikimate/quinate hydroxycinnamoyltransferase affects phenylpropanoid biosynthesis," *The Plant Cell*, 16:1446-1465, 2004.
Jung et al., "Characteristics of plant cell walls affecting intake and digestibility of forages by ruminants," *J. Anim. Sci.* 73:2774-2790, 1995.
Jung et al., "Genetic manipulation of cell walls—Identification of cell wall traits that can be manipulated to improve forage digestibility," U.S. Dairy Forage Research Center, 1996 Informational Conference with Dairy and Forage Industries, 1996.
Jung et al., "Influence of lignin on digestibility of forage cell wall material," *J. Anim. Sci.*, 62:1703-1712, 1986.
Lara, "Nation taking a closer look at fossil fuel alternatives," *Southwest Farm Press*, Nov. 3, 2005.
Lee et al., "Dilute-acid hydrolysis of lignocellulosic biomass," *Advances in Biochemical Engineering/Biotechnology*, 65:93-115, 1999.
Lewin, "Switchgrass: the super plant saviour?—President touts alternative fuel ingredient, but when will it be ready," Good Morning America, ABCNews.com, Feb. 1, 2006.
Lewis, "A 20th century roller coaster ride: a short account of lignification," *Current Opinion in Plant Biology*, 2:153-162, 1999.
Lynd et al., "Consolidated bioprocessing of cellulosic biomass: an update," *Current Opinion in Biotechnology*, 16:577-583, 2005.

McLaughlin et al., "Evaluating environmental consequences of producing herbaceous crops for bioenergy," *Biomass and Bioenergy*, 14(4):317-324, 1998.
McLaughlin et al., "Evaluating physical, chemical, and energetic properties of perennial grasses as biofuels," Proc. Bioenergy '96, The Seventh National Bioenergy Conference: Partnerships to Develop and Apply Biomass Technologies, Nashville, Tennessee, Sep. 15-20, 1996.
Muir et al., "Biomass production of 'alamo' switchgrass in response to nitrogen, phosphorus, and row spacing," *Agron. J.*, 93:896-901, 2001.
Olsson et al., "Fermentation of lignocellulosic hydrolysates for ethanol production," *Enzyme and Microbial Technology*, 18:312-331, 1996.
Pilate et al., "Field and pulping performances of transgenic trees with altered lignification," *Nature Biotechnology*, 20:607-612, 2002.
Pimentel et al., "Ethanol production using corn, switchgrass, and wood; Biodiesel production using soybean and sunflower," *Natural Resources Research*, 14(1):65-75, 2005.
Ralph et al., "Effects of coumarate 3-hydroxylase down-regulation on lignin structure," *J. Biol. Chem.*, 281(13):8843-8853, 2006.
Reddy et al., "Targeted down-regulation of cytochrome P450 enzymes for forage quality improvement in alfalfa (*Medicago sativa* L.)," *Proc. Nat. Acad. Sci.*, 102(46):16573-16578, 2005.
Richards et al., "Construction of a GFP-BAR plasmid and its use for switchgrass transformation," *Plant Cell Reports*, 20:48-54, 2001.
Sederoff et al., "Unexpected variation in lignin," *Current Opinion in Plant Biology*, 2:145-152, 1999.
Sederoff, "Building better trees with antisense," *Nature Biotechnology*, 17:750-751, 1999.
Shadle et al., "Effects of Down-regulation HCT on lignin in alfalfa," Phytochemical Society of North America Annual Meeting, Oxford, MS, Jul. 8-12, 2006.
Somleva et al., "Agrobacterium-mediated genetic transformation of switchgrass," *Crop Sci.*, 42:2080-2087, 2002.
Sticklen, "Plant genetic engineering to improve biomass characteristics for biofuels," *Current Opinion in Biotechnology*, 17:315-319, 2006.
Sun et al., "hydrolysis of lignocellulosic materials for ethanol production: a review," *Bioresource Technology*, 83:1-11, 2002.
Tabe et al., "Genetic engineering of grain and pasture legumes for improved nutritive value," *Genetica*, 90:181-200, 1993.
Talukder, "Low-lignin wood—a case study," *Nature Biotechnology*, 24(4):395-396, 2006.
Vogel et al., "Genetic improvement of switchgrass and other herbaceous plants for use as biomass fuel feedstock—Final Report," U.S. Department of Energy, Office of Fuels Development, Bioenergy Feedstock Development Program, Environmental Sciences Division, Oak Ridge National Laboratory, Oak Ridge Tennessee, 2000.
Whetten et al., "Genetic engineering of wood," *Forest Ecology and Management*, 43:301-316, 1991.
Wilson et al., "Genetics and properties of cellulases," *Advances in Biochemical Engineering/Biotechnology*, 65:1-21, 1999.
Wyman, "Biomass ethanol: technical progress, opportunities, and commercial challenges," *Annu. Rev. Energy Environ.*, 24:189-226, 1999.
Casler et al., "Genetic modification of lignin concentration affects fitness of perennial herbaceous plants," *Theor Appl Genet*, 104:127-131, 2002.
Chapple et al., "Loosening lignin's grip on biofuel production," *Nature Biotechnology*, 25(7):746-748, 2007.
Chen et al., "Lignin modification improves fermentable sugar yields for biofuel production," *Nature Biotechnology*, 25(7):759-761, 2007.
Dixon et al., "Expanding the utility of Alfalfa," *In Vitro Cellular & Developmental Biology Animal*, 42(Suppl. S.):15A, 2006.
EMBL Database Accession No. CA186689, dated Sep. 25, 2003.
EMBL Database Accession No. DN143567, dated Feb. 20, 2005.
Gressel et al., "Transgenics are imperative for biofuel crops," *Plant Science*, 174:246-263, 2008.
Nakashima et al., Down-regulation of key enzymes in the monolignol pathway effects on lignin composition in specific cell types of alfalfa (*Medicago sativa* L.), Phytochemical Society of North America, 2006 PSNA Annual Meeting, Oxford, Mississippi, Jul. 8-12, 2006.

(56) References Cited

OTHER PUBLICATIONS

Weng et al., "Emerging strategies of lignin engineering and degradation for cellulosic biofuel production," *Current Opinion in Biotechnology*, 19:166-172, 2008.

Baucher, M.D. et al. Biosynthesis and genetic engineering of lignin, *Crit. Rev. Plant. Sci.* 17:125-197, 1998.

Jung, H.G. et al. Impact of lignin composition on cell-wall degradability in an *Arabidopsis* mutant. *J. Sci. Food Agric.* 79:922-928, 1999.

Ni, W. et al. Reduced lignin in transgenic plants containing a caffeic acid O-methyltransferase antisense gene. *Transgenic Res.* 3:120-126, 1994.

* cited by examiner

FIG. 3
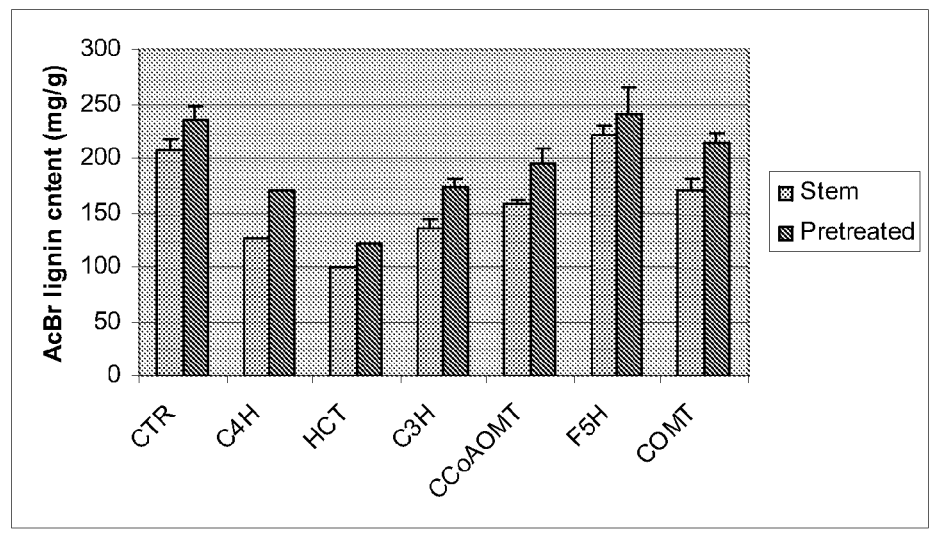
FIG. 3A
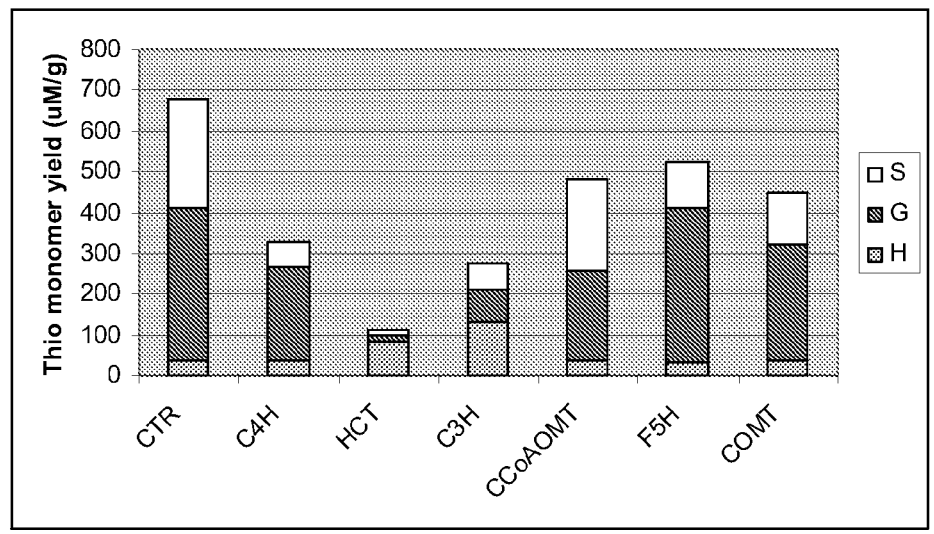
FIG. 3B

FIG. 5
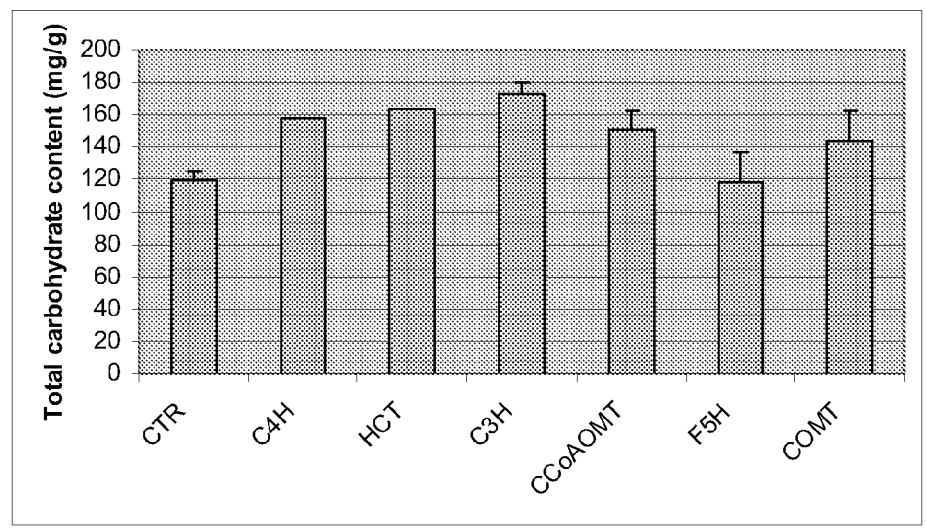
FIG. 5A
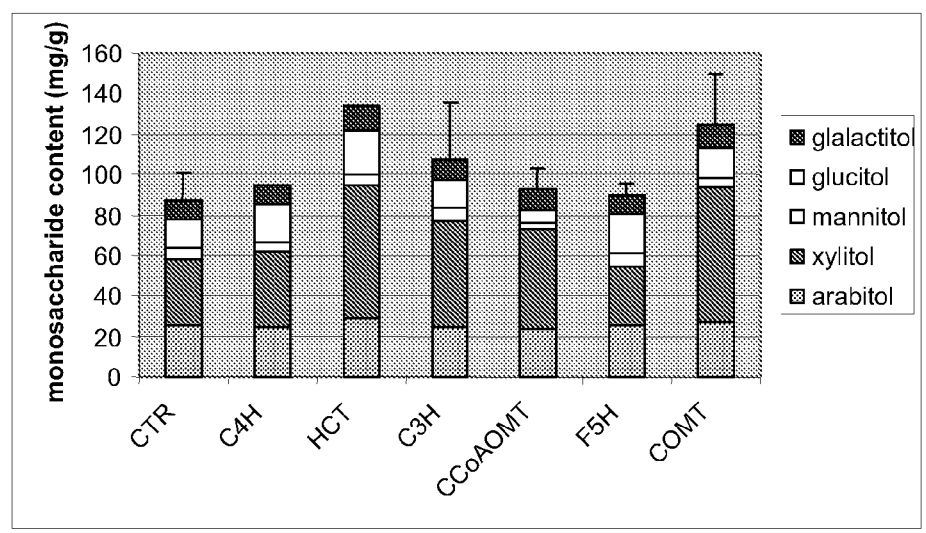
FIG. 5B

BIOFUEL PRODUCTION METHODS AND COMPOSITIONS

CROSS REFERENCE TO RELATED APPLICATIONS

This application claims the benefit of U.S. Provisional Patent Application Ser. No. 60/866,764, filed Nov. 21, 2006, the entire contents of which are herein specifically incorporated by reference.

BACKGROUND OF THE INVENTION

1. Field of the Invention

The present invention relates generally to agriculture and energy production. More specifically, the invention relates to methods and compositions for the production of biofuels from plants.

2. Description of the Related Art

Ethanol is increasingly being considered as a renewable, cleaner alternative to petroleum based fuels. Currently, Brazil and the United States are the two largest producers of ethanol, and each produce about four billion gallons of ethanol a year, with most of that production from sugar or starch crops: sugarcane in Brazil and corn in the United States. Ethanol may also be produced from lignocellulosic based biomass sourced from agricultural and forestry residues, urban waste, and biomass dedicated woody and grassy crops.

Of the crops that have been considered for use as lignocellulosic biomass, switchgrass (*Panicum virgatum*) has been identified as a particularly attractive candidate (McLaughlin and Walsh, 1998). Switchgrass is a perennial warm season grass native to the North American Tallgrass Prairie. Among its beneficial characteristics for use as a lignocellulosic biomass source crop are: high productivity, minimal nutrient needs, stand longevity, pest and disease resistance, water use efficiency, soil restoring properties, erosion control, wide geographic range, and adaptability to marginal soils. Other plants, including *Miscanthus×giganteus*, poplar, and more traditional forage crops such as alfalfa may also be of interest for production of lignocellulosic biomass. In each case, lignin in the biomass may interfere with the availability of cellulose and hemicellulose as sources of fermentable sugar.

The principal source of fermentable sugar in lignocellulosic biomass is cellulose. In typical lignocellulosic biomass used for ethanol production, cellulose accounts for between 35 to 50% of the mass. Cellulose is a long chain polysaccharide carbohydrate, composed of repeating cellobiose ($\beta$-1,4 glucose disaccharide) units. Hemicellulose also contributes to the fermentable sugar content of lignocellulosic biomass. It comprises about 20 to 35% of lignocellulosic biomass mass, and is a mixture of a variety of sugars including arabinose, galactose, glucose, mannose, and xylose, and derivatives of such sugars.

The third major component of lignocellulosic biomass, lignin, is not a sugar based fermentable polymer. Lignin is a complex polymer of hydroxylated and methoxylated phenylpropane units, linked via oxidative coupling that is probably catalyzed by both peroxidases and laccases (Boudet, et al., 1995), and comprises about 12 to 20% of lignocellulosic biomass. For ethanol production from lignocellulosic biomass, the cellulose and hemicellulose components are processed to produce their constituent sugars, and these sugars are then used to make ethanol via fermentation.

However, not only does lignin not contribute fermentable sugar to lignocellulosic biomass, but its presence also reduces the efficiency of enzymatic hydrolysis of cellulose, apparently by physically shielding the cellulose molecules from the hydrolytic enzymes. Consequently, chemical loosening of lignin from the lignocellulosic biomass is often one of the first steps in the ethanol production processes. This process consumes energy, and utilizes chemical treatments (e.g. hot acid) that require clean-up (e.g. neutralization and disposal of waste). There is currently no experimental evidence to indicate how lignin removal by directly engineering the plant may affect the various steps of bioethanol processing, i.e. pretreatment and enzymatic conversion of biomass in dedicated lignocellulosic biomass crops.

There has been considerable interest in the potential for genetic manipulation of lignin content and composition to improve the digestibility of forage crops and pulping properties of trees (Dixon, et al., 1994; Tabe, et al., 1993; Whetten and Sederoff, 1991; U.S. Patent Appl. Pub. 2004/0049802.). Small decreases in lignin content have been reported to positively impact the digestibility of forages (Casler, 1987). With respect of ethanol production, genetic modification to reduce or alter the lignin content of dedicated biomass crops might significantly improve the efficiency of cellulose hydrolysis, increasing the yield of fermentable sugars from the biomass (e.g. Sticklen, 2006). However it has not been clear whether it is lignin composition, lignin content, or both, that interferes with the availability of cellulose and hemicellulose and their constituent sugars for fermentation and biofuel production.

To date, there have been few published reports on the genetic modification of lignin in forage crops such as alfalfa, among others (e.g. Reddy et al., 2005; Guo et al., 2001). Most studies having concentrated on model systems such as *Arabidopsis* and tobacco (Hoffmann et al., 2004), or tree species such a poplar. Baucher et al. (2003) summarize effects of changes in lignin composition on pulp production from wood biomass. Davison et al. (2005) describe changes in the release of xylose following dilute acid hydrolysis of *Populus* biomass as a result of small variations in lignin content and composition in natural progeny of a cross. Thus the effect of such modifications on forage digestibility, and fermentability to produce ethanol, is unclear.

In one study, down-regulation of cinnamyl alcohol dehydrogenase led to a small but significant improvement in in vitro dry matter digestibility in transgenic alfalfa (Baucher, et al., 1999). U.S. Pat. No. 5,451,514 discloses a method of altering the content or composition of lignin in a plant by stably incorporating into the genome of the plant a recombinant DNA encoding an mRNA having sequence similarity to cinnamyl alcohol dehydrogenase. U.S. Pat. No. 5,850,020 discloses a method for modulating lignin content or composition by transforming a plant cell with a DNA construct with at least one open reading frame coding for a functional portion of one of several enzymes isolated from *Pinus radiata* (pine) or a sequence having 99% homology to the isolated gene: cinnamate 4-hydroxylase (C4H), coumarate 3-hydroxylase (C3H), phenolase (PNL), O-methyltransferase (OMT), cinnamoyl-CoA reductase (CCR), phenylalanine ammonia-lyase (PAL), 4-coumarate:CoA ligase (4CL), and peroxidase (POX).

U.S. Pat. No. 5,922,928 discloses a method of transforming and regenerating *Populus* species to alter the lignin content and composition using an O-methyltransferase gene. U.S. Pat. No. 6,610,908 describes manipulation of lignin composition in plants using a tissue-specific promoter and a sequence encoding a ferulate-5-hydroxylase (F5H) enzyme. Use of regulatory genes to modify the process of lignification in plants has also been described (e.g. U.S. Pat. No. 6,841,721 and U.S. Patent Publ. 20030005481). U.S. Pat. Applic. 20040049802 describes modification of plant lignin composition and increasing the in vivo digestibility of forages. WO 2006/012594 describes decreasing lignin content and improving lignin profiles in transgenic plants.

While the foregoing studies have provided a further understanding of the production of plant lignin, there remains a great need in the art for plants with improved cellulose and hemicellulose availability as a result of reduced lignin content or modified lignin composition, but the exact modifications necessary for improving cellulose and/or hemicellulose availability for saccharification are not clear based on currently available information. Development of such plants would have a significant benefit for the production of ethanol from plants.

SUMMARY OF THE INVENTION

In one aspect, the invention provides a transgenic plant of a biofuel crop species comprising a selected DNA that down regulates lignin biosynthesis in the plant and wherein the plant exhibits an increase in fermentable carbohydrates relative to a plant of the same genotype lacking the selected DNA. In one embodiment, the plant comprises a selected DNA that down regulates at least a first lignin biosynthesis gene selected from the group consisting of 4-coumarate 3-hydroxylase (C3H), phenylalanine ammonia-lyase (PAL), cinnamate 4-hydroxylase (C4H), hydroxycinnamoyl transferase (HCT), caffeic acid O-methyltransferase (COMT), caffeoyl CoA 3-O-methyltransferase (CCoAOMT), ferulate 5-hydroxylase (F5H), cinnamyl alcohol dehydrogenase (CAD), cinnamoyl CoA-reductase (CCR), 4-coumarate-CoA ligase (4CL), monolignol-lignin-specific glycosyltransferase, and aldehyde dehydrogenase (ALDH). In certain embodiments, at least two, at least three, or at least four of said lignin biosynthesis genes are down-regulated. The transgenic plant may further comprise a selected DNA that is an antisense or RNAi construct.

In particular embodiments, the transgenic plant may be defined as being from a species selected from the group consisting of switchgrass (*Panicum virgatum*), giant reed (*Arundo donax*), reed canarygrass (*Phalaris arundinacea*), Miscanthus×giganteus, Miscanthus sp., sericea lespedeza (*Lespedeza cuneata*), corn, sugarcane, sorghum, millet, ryegrass (*Lolium multiflorum, Lolium* sp.), timothy, Kochia (*Kochia scoparia*), forage soybeans, alfalfa, clover, sunn hemp, kenaf, bahiagrass, bermudagrass, dallisgrass, pangolagrass, big bluestem, indiangrass, fescue (*Festuca* sp.) including tall fescue, *Dactylis* sp., *Brachypodium distachyon*, smooth bromegrass, orchardgrass, Kentucky bluegrass, and poplar (*Populus* sp.). In certain embodiments, the transgenic plant may further be defined as a monocot. In a particular embodiment, the transgenic plant may be switchgrass. In another embodiment, the transgenic plant may be further defined as a dicot. In a particular embodiment, the transgenic plant may be alfalfa. The transgenic plant comprising an antisense or RNAi construct may comprise a promoter selected from the group consisting of a developmentally-regulated, organelle-specific, inducible, tissue-specific, constitutive, cell-specific, seed specific, or germination-specific promoter.

In another embodiment, the transgenic plant may be further defined as an R0 transgenic plant, or as a progeny plant of any generation of an R0 transgenic plant, wherein the transgenic plant has inherited the selected DNA from the R0 transgenic plant. In other embodiments, the invention comprises a seed of a transgenic plant wherein the seed comprises a selected DNA that down regulates at least a first lignin biosynthesis gene. A transgenic cell of such a plant also comprises an embodiment of the invention.

In another aspect, the invention comprises a method of increasing the level of fermentable carbohydrates in a biofuel crop species plant by down-regulating in the plant at least a first lignin biosynthesis gene. In certain embodiments the invention comprises such a method, wherein the down-regulating is accomplished by introduction of an isolated nucleic acid sequence that encodes all or part of a lignin biosynthesis gene or its complement. In some embodiments the isolated nucleic acid sequence is in sense orientation. The fermentable carbohydrate(s) may be selected from the group consisting of xylose, arabinose, mannose, glucose, xyloglucan, arabinoglucan, galacturonan, starch, and cellobiose.

In other embodiments the method for down-regulating a lignin biosynthesis gene comprises mutating a lignin biosynthesis gene. The method may also comprise one wherein the isolated nucleic acid sequence is an antisense or RNAi construct, or wherein the isolated nucleic acid sequence encodes a ribozyme or zinc-finger protein that inhibits the expression of the lignin biosynthesis gene. In particular embodiments, the method may be defined as one wherein the down-regulating comprises introducing into the plant a selected DNA that down regulates at least a first enzyme activity selected from the group consisting of: 4-coumarate 3-hydroxylase (C3H), phenylalanine ammonia-lyase (PAL), cinnamate 4-hydroxylase (C4H), hydroxycinnamoyl transferase (HCT) caffeic acid O-methyltransferase (COMT), caffeoyl coA 3-O-methyltransferase (CCoAOMT), ferulate 5-hydroxylase (F5H), cinnamyl alcohol dehydrogenase (CAD), cinnamoyl CoA-reductase (CCR), 4-coumarate-CoA ligase (4CL), monolignol-lignin-specific glycosyltransferase, and aldehyde dehydrogenase (ALDH).

In certain embodiments, introducing the isolated or selected nucleic acid comprises plant breeding. In other embodiments, introducing the isolated nucleic acid comprises genetic transformation. In specific embodiments of the method, the plant is from a species selected from the group consisting of: switchgrass (*Panicum virgatum*), giant reed (*Arundo donax*), reed canarygrass (*Phalaris arundinacea*), Miscanthus×giganteus, Miscanthus sp., sericea lespedeza (*Lespedeza cuneata*), corn, sugarcane, sorghum, millet, ryegrass (*Lolium multiflorum, Lolium* sp.), timothy, Kochia (*Kochia scoparia*), forage soybeans, alfalfa, clover, sunn hemp, kenaf, bahiagrass, bermudagrass, dallisgrass, pangolagrass, big bluestem, indiangrass, fescue (*Festuca* sp.), *Dactylis* sp., *Brachypodium distachyon*, smooth bromegrass, orchardgrass, Kentucky bluegrass, and poplar. In certain embodiments, the plant is a monocot. In particular embodiments, the plant is further defined as switchgrass. In yet other embodiments, the plant is further defined as a dicot. In yet other particular embodiments, the plant is an alfalfa plant.

In yet another aspect, the invention provides a method of producing ethanol comprising: (a) obtaining a plant of a biofuel crop species comprising a selected DNA that down regulates lignin biosynthesis in the plant and wherein the plant exhibits an increase in fermentable carbohydrates relative to a plant of the same genotype lacking the selected DNA; (b) treating tissue from the plant to render carbohydrates in the tissue fermentable; and (c) fermenting the carbohydrates to produce ethanol.

In yet another aspect, the invention provides a method for processing lignocellulosic biomass from a plant species, wherein the biomass comprises reduced lignin content, as a result of the presence of a transgenic nucleic acid sequence or through a classical selection and breeding process, relative to that typically found in biomass material obtained from plants of the plant species that do not comprise the transgenic sequence or have not undergone such a selection and breeding process, and wherein at least 30%, at least 40%, or at least 50% of the total sugars present in the starting lignocellulosic material are released from the material as a result of the process (calculated on a w/w basis).

In one embodiment the method for processing lignocellulosic biomass from a plant species, wherein the biomass comprises reduced lignin content as a result of the presence of a transgenic nucleic acid sequence, may comprise acid and/or enzymatic treatment(s). The enzymatic treatment may comprise treatment with one or more cellulolytic enzymes, such as a cellulase. In another embodiment, the method comprises an acid treatment prior to or during a treatment to render carbohydrates in the plant fermentable. In yet another embodiment, no acid treatment is performed. In other embodiments, the transgenic sequence present in the plant material down-regulates expression of HCT, C4H, or C3H.

In other embodiments, the invention provides a recombinant vector comprising an antisense or RNAi construct comprising sequences homologous to one or more lignin biosynthesis gene selected from C3H, PAL, C4H, HCT, F5H, C4H, COMT, CCoAOMT, CAD, CCR, 4CL, or ALDH, including all possible combination thereof, as well as plants transformed with these sequences. Also provided by the invention are nucleic acids encoding the polypeptides encoded by these sequences, and nucleic acids corresponding to partial coding sequences. In a particular embodiment, a nucleotide sequence of the HCT gene of switchgrass (SEQ ID NO:10), or its complement, may be utilized.

Thus, in certain embodiments of the invention, nucleic acids hybridizing to such sequences, including SEQ ID NO:10, or its complement, under stringent conditions are provided. Stringent conditions may be defined as 5×SSC, 50% formamide and 42° C. By conducting a wash under such conditions, for example, for 10 minutes, those sequences not hybridizing to a particular target sequence under these conditions can be removed. Provided in still further embodiments of the invention are sequences having at least 95%, 90%, 85%, or 75% sequence identity to the nucleic acid sequence of SEQ ID NO:10 or its complement.

Nucleic acids provided by the invention include those comprising fragments of lignin biosynthesis genes in sense and/or antisense orientation. Those of skill in the art will immediately understand in view of the disclosure that such fragments may readily be prepared by placing fragments of lignin biosynthesis coding sequences in frame in an appropriate expression vector, for example, comprising a plant promoter. Using the methods described in the working examples, lignin biosynthesis activity and down-regulation can be efficiently confirmed for any given fragment. Fragments of nucleic acids may be prepared according to any of the well known techniques including partial or complete restriction digests and manual shearing.

Nucleic acid sequences may be provided operably linked to a heterologous promoter, in sense or antisense orientation. Expression constructs are also provided comprising these sequences, including antisense and RNAi oligonucleotides thereof, as are plants and plant cells transformed with the sequences. The construction of vectors which may be employed in conjunction with plant transformation techniques using these or other sequences according to the invention will be known to those of skill of the art in light of the present disclosure (see, for example, Sambrook et al., 1989; Gelvin et al., 1990). The techniques of the current invention are thus not limited to any particular nucleic acid sequences.

BRIEF DESCRIPTION OF THE DRAWINGS

The following drawings form part of the present specification and are included to further demonstrate certain aspects of the invention. The invention may be better understood by reference to one or more of these drawings in combination with the detailed description of specific embodiments presented herein:

FIG. 3. Lignin content of dilute acid pre-treated and non-pretreated alfalfa stems determined by the acetyl bromide method.

FIGS. 5A-C. (A) Carbohydrate content of hydrolysate from control and lignin-modified transgenic lines following dilute acid hydrolysis pre-treatment. (B) Individual sugars present in the acid hydrolysates analyzed by GC/MS. (C) Glucose and xylose content of enzymatic hydrolysates of acid-pretreated material, as determined by HPLC.

DETAILED DESCRIPTION OF THE INVENTION

Figure 1:
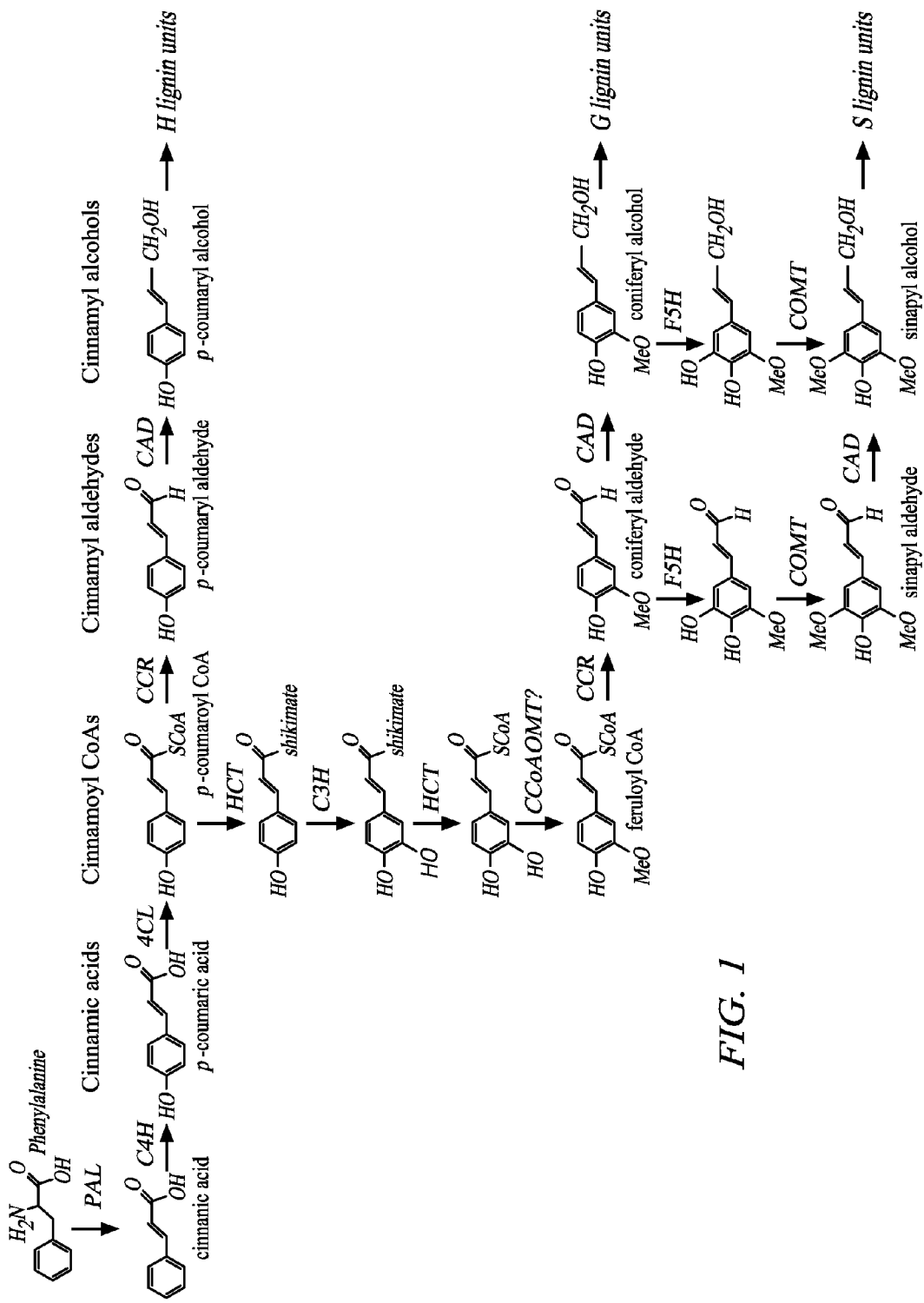
FIG. 1. Schematic diagram illustrating the plant lignin biosynthesis pathway.

The invention overcomes the limitations of the prior art by providing improved methods and compositions for the production of ethanol from plants with low, reduced, or modified lignin content. The invention is significant in that lignin, while imparting mechanical strength to plant stems and trunks, and hydrophobicity to water conducting vascular elements, negatively impacts the availability of cellulose and other carbohydrates for enzymatic hydrolysis during the production of ethanol from the plant. Decreasing the lignin content of plants may therefore be used to significantly benefit the production of ethanol by increasing the yield of fermentable carbohydrates. An increase in the level of fermentable carbohydrate in a lignin-reduced crop, as compared to the level found in an otherwise similar crop lacking the modification in its lignin biosynthesis pathway, is demonstrated for the first time. Saccharification efficiency is thus improved, even allowing omission of acid pre-treatment for processing biomass with reduced lignin levels.

Lignins contain three major monomer species, termed p-hydroxyphenyl (H), guaiacyl (G) and syringyl (S), produced by reduction of CoA thioesters of coumaric, ferulic and sinapic acids, respectively. In angiosperms, guaiacyl and syringyl units predominate, and the S/G ratio affects the physical properties of the lignin. The S and G units are linked through at least five different dimer bonding patterns (Davin, and Lewis, 1992). The mechanisms that determine the relative proportions of these linkage types in a particular lignin polymer have been unknown. Furthermore, there is considerable debate as to whether lignin composition and structure are tightly controlled, or are flexible depending upon monomer availability (Lewis, 1999; Sederoff, et al., 1999).

Although a number of studies have linked decreased forage digestibility to increased S/G ratio as a function of increased maturity (Jung and Vogel, 1986; Buxton, and Russell, 1988; Grabber, et al., 1992), other studies have questioned the effect of lignin composition on digestibility (Grabber, et al., 1997; Reddy et al., 2005). Further, the hardwood gymnosperm lignins are highly condensed, essentially lacking S residues, and this makes them less amenable to chemical pulping, in apparent contradiction to the concept that reducing S/G ratio would be beneficial for forage digestibility. The reported lack of agreement in the relationship of lignin composition to forage digestibility and chemical pulping is partly due to the fact that the studies to date either have been in vitro, or have compared plant materials at different developmental stages, different varieties or even different species. Further, the degree to which the conclusions of studies relating to the effect of lignin content and composition regarding forage digestibility and pulping can be extended to the fermentation of lignocellulosic biomass for production of ethanol remains unclear.

Plants that may be genetically modified resulting in modified (e.g. reduced) lignin content for ethanol production from lignocellulosic biomass in accordance with the invention may include switchgrass (*Panicum virgatum*), giant reed (*Arundo donax*), reed canarygrass (*Phalaris arundinacea*), Miscanthus×giganteus, *Miscanthus* sp., sericea lespedeza (*Lespedeza cuneata*), corn, sugarcane, sorghum, millet, ryegrass (*Lolium multiflorum, Lolium* sp.), timothy, Kochia (*Kochia scoparia*), forage soybeans, alfalfa, clover, sunn hemp, kenaf, bahiagrass, bermudagrass, dallisgrass, pangolagrass, big bluestem, indiangrass, fescue (*Festuca* sp.), *Dactylis* sp., *Brachypodium distachyon*, smooth bromegrass, orchardgrass, Kentucky bluegrass, and poplar, among others.

Studies were conducted aimed at determining the effects of down-regulating genes involved in the lignin biosynthetic pathway (FIG. 1) in biofuel crop plants, namely 4-coumarate 3-hydroxylase (C3H), phenylalanine ammonia-lyase (PAL), cinnamate 4-hydroxylase (C4H), hydroxycinnamoyl transferase (HCT), ferulate 5-hydroxylase (F5H), caffeic acid O-methyltransferase (COMT), and caffeoyl coA 3-O-methyltransferase (CCoAOMT), and specifically in relation to their impact on the biomass availability of cellulosic compounds and hence carbohydrates for fermentation to ethanol. Both lignin content and composition were measured in transgenic plants down-regulated for each of the lignin synthesis pathway genes. Yields of fermentable carbohydrates (e.g. glucose, xylose) were then determined from samples that may or may not have been further subjected to further processing steps, including a dilute acid hydrolysis treatment step, and/or cellulase treatment.

The lignin biosynthesis pathway (FIG. 1) starts with the conversion of phenylalanine to cinnamate by phenylalanine ammonia lyase (PAL). The second reaction is performed by cinnamate 4-hydroxylase (C4H) which converts cinnamate to 4-coumarate. These two enzymes form the core of the phenylpropanoid pathway including lignin biosynthesis. Other enzymes in the pathway include C3H or 4-coumarate 3-hydroxylase, which converts 4-coumaroyl shikimate or quinate to caffeoyl shikimate or quinate; HCT, hydroxycinnamoyl CoA: hydroxycinnamoyl transferase which acts at two places: catalyzing the formation of 4-coumaroyl shikimate (or quinate), the substrate for C3H, from 4-coumaroyl CoA, and also acting in the opposite direction on caffeoyl shikimate (or quinate), to yield caffeoyl CoA.

CCoAOMT converts caffeoyl CoA to feruloyl coA and might also be involved in other reactions. COMT or caffeic acid O-methyl transferase acts on 5-hydroxy coniferaldehyde and converts it into sinapaldehyde. This enzyme also could act on several other substrates in vitro but it is not clear if it acts on them in vivo. Ferulate 5-hydroxylase (F5H) converts coniferaldehyde to 5-hydroxyconiferaldehyde.

Monomethylated guaiacyl units derived from coniferyl alcohol and dimethylated syringyl units derived from sinapyl alcohol are the major monolignols in alfalfa and other angiosperms. In addition p-hydroxyphenyl units are also present in trace amounts. These monolignols can be designated as H lignin, G lignin and S lignin. These may be analyzed by H/T and S/G ratio where T represents total lignin content. Since the H lignin is in trace amounts, H/T ratios are usually very low in alfalfa, around 0.02 to 0.04. Similarly, the S/G ratio is around 0.5 and changes (increases) as the stem matures.

S/G ratio has been negatively correlated with digestibility but there are contradictory reports available as well. Lignin composition changes with advanced maturity towards a progressively higher S/G ratio. Higher G lignin is not good for pulping. For example the softwood gymnosperms essentially lack S lignin units and are less amenable for pulping compared to angiosperm lignin. Observations of pulping efficiency parameters had suggested that an increase in S/G lignin ratio is important for improving chemical degradability of lignin. The paper pulping model does not apparently apply to digestion of cell wall material by rumen microorganisms, since there was no relationship between S/G ratio and digestibility. In contrast, total lignin content was highly correlated with digestibility (Reddy et al., 2005). Additionally, manipulation of H lignin levels in a lignocellulosic feedstock could assist in gasification of the biomass.

Antisense constructs for down-regulating each of C3H, PAL, C4H, HCT, COMT, CCoaOMT, and F5H were introduced into alfalfa and switchgrass, and stably transformed plant lines are selected, for instance using kanamycin as a selectable marker. Lignin content and compositional changes were observed in alfalfa. For example the C3H and HCT down-regulated lines showed similar lignin compositional changes which were basically an increase in the H/Total lignin ratio and decrease in the lignin content. Yields of fermentable carbohydrates were also determined in samples from these lines. The results demonstrate the effectiveness of the invention in enhancing the yield of fermentable carbohydrates in a crop useful for biomass production.

In accordance with the invention, down-regulation of lignin biosynthesis genes may be used to decrease lignin content and alter lignin composition to improve availability of carbohydrate compounds, and other characteristics. For example, by introducing an antisense, RNAi or other desired coding sequence to down-regulate a lignin biosynthesis gene as described herein, improvements in fermentability may be obtained. In one embodiment of the invention plant transformation constructs are provided encoding one or more lignin biosynthesis coding sequence for expression in a biomass crop such as switchgrass. Such lignin biosynthesis genes are known and may be from, for example, alfalfa, barley, sunflower, loblolly pine, maize, potato, rice, rye, sugarcane, sorghum, soybean, switchgrass, tomato, wheat and *Medicago truncatula*.

One aspect of the invention therefore relates to a recombinant vector comprising an antisense or RNAi construct comprising sequences homologous to one or more lignin biosynthesis gene(s) selected from C3H, PAL, C4H, HCT, COMT, CCoAOMT, F5H, CAD, CCR, 4CL, ALDH, and monolignol-lignin-specific glycosyltransferase, including all possible combination thereof, and which decreases the expression of at least one of the mentioned lignin biosynthesis genes, as well as a plant of a biofuel crop species transformed with these sequences. In a particular embodiment, the recombinant vector comprises nucleotide sequences encoding HCT from switchgrass (e.g. SEQ ID NO:10). Also provided by the invention are nucleic acids encoding the polypeptides encoded by these sequences. Homologous or orthologous lignin biosynthesis related sequences from other species, such as *Miscanthus*, may also be identified and used in the corresponding species to down-regulate lignin synthesis and increase the availability of fermentable carbohydrates.

Sequences that hybridize to any of these sequences under stringent conditions may be used to identify further sequences to down-regulate lignin biosynthesis. An example of such conditions is 5×SSC, 50% formamide and 42° C. It will be understood by those of skill in the art that stringency conditions may be increased by increasing temperature, such as to about 60° C. or decreasing salt, such as to about 1×SSC, or may be decreased by increasing salt, for example to about 10×SSC, or decreasing temperature, such as to about 25° C.

Nucleic acids provided by the invention include those comprising fragments of lignin biosynthesis genes in sense and/or antisense orientation. Those of skill in the art will immediately understand in view of the disclosure that such fragments may readily be prepared by placing fragments of lignin biosynthesis coding sequences in frame in an appropriate expression vector, for example, comprising a plant promoter. Using the methods described in the working examples, lignin biosynthesis activity and down-regulation can be efficiently confirmed for any given fragment. Fragments of nucleic acids may be prepared according to any of the well known techniques including partial or complete restriction digests and manual shearing.

Nucleic acid sequences may be provided operably linked to a heterologous promoter, in sense or antisense orientation. Expression constructs are also provided comprising these sequences, including antisense and RNAi oligonucleotides thereof, as are plants and plant cells transformed with the sequences. The construction of vectors which may be employed in conjunction with plant transformation techniques using these or other sequences according to the invention will be known to those of skill of the art in light of the present disclosure (see, for example, Sambrook et al., 1989; Gelvin et al., 1990). The techniques of the current invention are thus not limited to any particular nucleic acid sequences.

One important use of the sequences provided by the invention will be in the alteration of plant phenotypes by genetic transformation with constructs comprising sequences homologous to lignin biosynthesis coding sequences, for example, one or more of C3H, PAL, C4H, HCT, COMT, CCoAOMT, and F5H. Nucleic acids encoding C3H, PAL, C4H, HCT, COMT, CCoAOMT, and F5H are known in the art and are disclosed in, for example, U.S. Pat. No. 5,850,020, the entire disclosure of which is specifically incorporated herein by reference.

These sequences may be provided with other sequences for efficient expression as is known in the art. One or more selectable marker genes may be co-introduced into a plant with a nucleic acid provided by the invention. The choice of any additional elements used in conjunction with a sequence will often depend on the purpose of the transformation. One of the major purposes of transformation of crop plants is to add commercially desirable, agronomically important traits to the plant, as described above.

I. Production of Ethanol from Lignocellulosic Biomass

The overall process for the production of ethanol from biomass typically involves two steps: saccharification and fermentation. First, saccharification produces fermentable sugars from the cellulose and hemicellulose in the lignocellulosic biomass. Second, those sugars are then fermented to produce ethanol. Thorough, detailed discussion of additional methods and protocols for the production of ethanol from biomass are reviewed in Wyman (1999); Gong, et al. (1999); Sun and Cheng, (2002); and Olsson and Hahn-Hagerdal (1996).

A. Pretreatment

Raw biomass is typically pretreated to increase porosity, hydrolyze hemicellulose, remove lignin and reduce cellulose crystallinity, all in order to improve recovery of fermentable sugars from the cellulose polymer. As a preliminary step in pretreatment, the lignocellulosic material may be chipped or ground. The size of the biomass particles after chipping or grinding is typically between 0.2 and 30 mm. After chipping a number of other pretreatment options may be used to further prepare the biomass for saccharification and fermentation, including steam explosion, ammonia fiber explosion, acid hydrolysis.

1. Steam Explosion

Steam explosion is a very common method for pretreatment of lignocellulosic biomass and increases the amount of cellulose available for enzymatic hydrolysis (U.S. Pat. No. 4,461,648). Generally, the material is treated with high-pressure saturated steam and the pressure is rapidly reduced, causing the materials to undergo an explosive decompression. Steam explosion is typically initiated at a temperature of 160-260° C. for several seconds to several minutes at pressures of up to 4.5 to 5 MPa. The biomass is then exposed to atmospheric pressure. The process causes hemicellulose degradation and lignin transformation. Addition of $H_2SO_4$, $SO_2$, or $CO_2$ to the steam explosion reaction can improve subsequent cellulose hydrolysis, decrease production of inhibitory compounds and lead to the more complete removal of hemicellulose (Morjanoff and Gray, 1987).

2. Ammonia Fiber Explosion (AFEX)

In AFEX pretreatment, the biomass is treated with approximately 1-2 kg ammonia per kg dry biomass for approximately 30 minutes at pressures of 1.5 to 2 MPa. (U.S. Pat. No. 4,600,590; U.S. Pat. No. 5,037,663; Mes-Hartree, et al. 1988). Like steam explosion, the pressure is then rapidly reduced to atmospheric levels, boiling the ammonia and exploding the lignocellulosic material. AFEX pretreatment appears to be especially effective for biomass with a relatively low lignin content, but not for biomass with high lignin content such as newspaper or aspen chips (Sun and Cheng, 2002).

3. Acid Hydrolysis

Concentrated or dilute acids may also be used for pretreatment of lignocellulosic biomass. $H_2SO_4$ and HCl have been used at high, >70%, concentrations. In addition to pretreatment, concentrated acid may also be used for hydrolysis of cellulose (U.S. Pat. No. 5,972,118). Dilute acids can be used at either high (>160° C.) or low (<160° C.) temperatures, although high temperature is preferred for cellulose hydrolysis (Sun and Cheng, 2002). $H_2SO_4$ and HCl at concentrations of 0.3 to 2% (w/w) and treatment times ranging from minutes to 2 hours or longer can be used for dilute acid pretreatment.

Other pretreatments include alkaline hydrolysis, oxidative delignification, organosolv process, or biological pretreatment; see Sun and Cheng (2002).

B. Saccharification

After pretreatment, the cellulose in the lignocellulosic biomass may be hydrolyzed with cellulase enzymes. Cellulase catalyzes the breakdown of cellulose to release glucose which can then be fermented into ethanol.

Bacteria and fungi produce cellulases suitable for use in ethanol production (Duff and Murray, 1995). For example, *Cellulomonas fimi* and *Thermomonospora fusca* have been extensively studied for cellulase production. Among fungi, members of the *Trichoderma* genus, and in particular *Trichoderma reesi*, have been the most extensively studied. Numerous cellulases are available from commercial sources as well. Cellulases are usually actually a mixture of several different specific activities. First, endoglucanases create free chain ends of the cellulose fiber. Exoglucanases remove cellobiose units from the free chain ends and beta-glucosidase hydrolyzes cellobiose to produce free glucose.

Reaction conditions for enzymatic hydrolysis are typically around pH 4.8 at a temperature between 45 and 50° C. with incubations of between 10 and 120 hours. Cellulase loading can vary from around 5 to 35 filter paper units (FPU) of activity per gram of substrate Surfactants like Tween 20, 80, polyoxyethylene glycol or Tween 81 may also be used during enzyme hydrolysis to improve cellulose conversion. Additionally, combinations or mixtures of available cellulases and other enzymes may also lead to increased saccharification.

Aside from enzymatic hydrolysis, cellulose may also be hydrolyzed with weak acids or hydrochloric acid (Lee et al., 1999).

C. Fermentation

Once fermentable sugars have been produced from the lignocellulosic biomass, those sugars may be used to produce ethanol via fermentation. Fermentation processes for producing ethanol from lignocellulosic biomass are extensively reviewed in Olsson and Hahn-Hagerdal (1996). Briefly, for maximum efficiencies, both pentose sugars from the hemicellulose fraction of the lignocellulosic material (e.g. xylose) and hexose sugars from the cellulose fraction (e.g. glucose) should be utilized. *Saccharomyces cerevisiae* are widely used for fermentation of hexose sugars. Pentose sugars, released from the hemicellulose portion of the biomass, may be fermented using genetically engineered bacteria, including *Escherichia coli* (U.S. Pat. No. 5,000,000) or *Zymomonas mobilis* (Zhang et al., 1995). Fermentation with yeast strains is typically optimal around temperatures of 30 to 37° C.

D. Simultaneous Saccharification and Fermentation (SSF)

Cellulase activity is inhibited by its end products, cellobiose and glucose. Consequently, as saccharification proceeds, the build up of those end products increasingly inhibits continued hydrolysis of the cellulose substrate. Thus, the fermentation of sugars as they are produced in the saccharification process leads to improved efficiencies for cellulose utilization (e.g. U.S. Pat. No. 3,990,944). This process is known as simultaneous saccharification and fermentation (SSF), and is an alternative to the above described separate saccharification and fermentation steps. In addition to increased cellulose utilization, SSF also eliminates the need for a separate vessel and processing step. The optimal temperature for SSF is around 38° C., which is a compromise between the optimal temperatures of cellulose hydrolysis and sugar fermentation. SSF reactions can proceed up to 5 to 7 days.

E. Distillation

The final step for production of ethanol is distillation. The fermentation or SSF product is distilled using conventional methods producing ethanol, for instance 95% ethanol.

II. Plant Transformation Constructs

Vectors used for plant transformation may include, for example, plasmids, cosmids, YACs (yeast artificial chromosomes), BACs (bacterial artificial chromosomes) or any other suitable cloning system, as well as fragments of DNA therefrom. Thus when the term "vector" or "expression vector" is used, all of the foregoing types of vectors, as well as nucleic acid sequences isolated therefrom, are included. It is contemplated that utilization of cloning systems with large insert capacities will allow introduction of large DNA sequences comprising more than one selected gene. In accordance with the invention, this could be used to introduce genes corresponding to an entire biosynthetic pathway into a plant. Introduction of such sequences may be facilitated by use of bacterial or yeast artificial chromosomes (BACs or YACs, respectively), or even plant artificial chromosomes. For example, the use of BACs for *Agrobacterium*-mediated transformation was disclosed by Hamilton et al. (1996).

Particularly useful for transformation are expression cassettes which have been isolated from such vectors. DNA segments used for transforming plant cells will, of course, generally comprise the cDNA, gene or genes which one desires to introduce into and have expressed in the host cells. These DNA segments can further include structures such as promoters, enhancers, polylinkers, or even regulatory genes as desired. The DNA segment or gene chosen for cellular introduction will often encode a protein which will be expressed in the resultant recombinant cells resulting in a screenable or selectable trait and/or which will impart an improved phenotype to the resulting transgenic plant. However, this may not always be the case, and the present invention also encompasses transgenic plants incorporating non-expressed transgenes. Preferred components likely to be included with vectors used in the current invention are as follows.

A. Regulatory Elements

Exemplary promoters for expression of a nucleic acid sequence include plant promoter such as the CaMV 35S promoter (Odell et al., 1985), or others such as CaMV 19S (Lawton et al., 1987), nos (Ebert et al., 1987), Adh (Walker et al., 1987), sucrose synthase (Yang and Russell, 1990), a-tubulin, actin (Wang et al., 1992), cab (Sullivan et al., 1989), PEPCase (Hudspeth and Grula, 1989) or those associated with the R gene complex (Chandler et al., 1989). Tissue specific promoters such as root cell promoters (Conkling et al., 1990) and tissue specific enhancers (Fromm et al., 1986) are also contemplated to be useful, as are inducible promoters such as ABA- and turgor-inducible promoters. The PAL2 promoter may in particular be useful with the invention (U.S. Pat. Appl. Pub. 2004/0049802, the entire disclosure of which is specifically incorporated herein by reference). In one embodiment of the invention, the native promoter of a lignin biosynthesis coding sequence is used.

The DNA sequence between the transcription initiation site and the start of the coding sequence, i.e., the untranslated leader sequence, can also influence gene expression. One may thus wish to employ a particular leader sequence with a transformation construct of the invention. Preferred leader sequences are contemplated to include those which comprise sequences predicted to direct optimum expression of the attached gene, i.e., to include a preferred consensus leader sequence which may increase or maintain mRNA stability and prevent inappropriate initiation of translation. The choice of such sequences will be known to those of skill in the art in light of the present disclosure. Sequences that are derived from genes that are highly expressed in plants will typically be preferred.

It is contemplated that vectors for use in accordance with the present invention may be constructed to include an ocs enhancer element. This element was first identified as a 16 bp palindromic enhancer from the octopine synthase (ocs) gene of *Agrobacterium* (Ellis et al., 1987), and is present in at least 10 other promoters (Bouchez et al., 1989). The use of an enhancer element, such as the ocs element and particularly multiple copies of the element, may act to increase the level of transcription from adjacent promoters when applied in the context of plant transformation.

It is envisioned that lignin biosynthesis coding sequences may be introduced under the control of novel promoters or enhancers, etc., or homologous or tissue specific promoters or control elements. Vectors for use in tissue-specific targeting of genes in transgenic plants will typically include tissue-specific promoters and may also include other tissue-specific control elements such as enhancer sequences. Promoters which direct specific or enhanced expression in certain plant tissues will be known to those of skill in the art in light of the present disclosure. These include, for example, the rbcS promoter, specific for green tissue; the ocs, nos and mas promoters which have higher activity in roots or wounded leaf tissue.

B. Terminators

Transformation constructs prepared in accordance with the invention will typically include a 3' end DNA sequence that acts as a signal to terminate transcription and allow for the poly-adenylation of the mRNA produced by coding sequences operably linked to a promoter. In one embodiment of the invention, the native terminator of a lignin biosynthesis coding sequence is used. Alternatively, a heterologous 3' end may enhance the expression of sense or antisense lignin biosynthesis coding sequences. Examples of terminators that are deemed to be useful in this context include those from the nopaline synthase gene of *Agrobacterium tumefaciens* (nos 3' end) (Bevan et al., 1983), the terminator for the T7 transcript from the octopine synthase gene of *Agrobacterium tumefaciens*, and the 3' end of the protease inhibitor I or II genes from potato or tomato. Regulatory elements such as an Adh intron (Callis et al., 1987), sucrose synthase intron (Vasil et al., 1989) or TMV omega element (Gallie et al., 1989), may further be included where desired.

C. Transit or Signal Peptides

Sequences that are joined to the coding sequence of an expressed gene, which are removed post-translationally from the initial translation product and which facilitate the transport of the protein into or through intracellular or extracellular membranes, are termed transit (usually into vacuoles, vesicles, plastids and other intracellular organelles) and signal sequences (usually to the endoplasmic reticulum, golgi apparatus and outside of the cellular membrane). By facilitating the transport of the protein into compartments inside and outside the cell, these sequences may increase the accumulation of gene product protecting them from proteolytic degradation. These sequences also allow for additional mRNA sequences from highly expressed genes to be attached to the coding sequence of the genes. Since mRNA being translated by ribosomes is more stable than naked mRNA, the presence of translatable mRNA in front of the gene may increase the overall stability of the mRNA transcript from the gene and thereby increase synthesis of the gene product. Since transit and signal sequences are usually post-translationally removed from the initial translation product, the use of these sequences allows for the addition of extra translated sequences that may not appear on the final polypeptide. It further is contemplated that targeting of certain proteins may be desirable in order to enhance the stability of the protein (U.S. Pat. No. 5,545,818, incorporated herein by reference in its entirety).

Additionally, vectors may be constructed and employed in the intracellular targeting of a specific gene product within the cells of a transgenic plant or in directing a protein to the extracellular environment. This generally will be achieved by joining a DNA sequence encoding a transit or signal peptide sequence to the coding sequence of a particular gene. The resultant transit, or signal, peptide will transport the protein to a particular intracellular, or extracellular destination, respectively, and will then be post-translationally removed.

D. Marker Genes

By employing a selectable or screenable marker protein, one can provide or enhance the ability to identify transformants. "Marker genes" are genes that impart a distinct phenotype to cells expressing the marker protein and thus allow such transformed cells to be distinguished from cells that do not have the marker. Such genes may encode either a selectable or screenable marker, depending on whether the marker confers a trait which one can "select" for by chemical means, i.e., through the use of a selective agent (e.g., a herbicide, antibiotic, or the like), or whether it is simply a trait that one can identify through observation or testing, i.e., by "screening" (e.g., the green fluorescent protein). Of course, many examples of suitable marker proteins are known to the art and can be employed in the practice of the invention.

Included within the terms "selectable" or "screenable" markers also are genes which encode a "secretable marker" whose secretion can be detected as a means of identifying or selecting for transformed cells. Examples include markers which are secretable antigens that can be identified by antibody interaction, or even secretable enzymes which can be detected by their catalytic activity. Secretable proteins fall into a number of classes, including small, diffusible proteins detectable, e.g., by ELISA; small active enzymes detectable in extracellular solution (e.g., α-amylase, β-lactamase, phosphinothricin acetyltransferase); and proteins that are inserted or trapped in the cell wall (e.g., proteins that include a leader sequence such as that found in the expression unit of extensin or tobacco PR-S).

Many selectable marker coding regions are known and could be used with the present invention including, but not limited to, neo (Potrykus et al., 1985), which provides kanamycin resistance and can be selected for using kanamycin, G418, paromomycin, etc.; bar, which confers bialaphos or phosphinothricin resistance; a mutant EPSP synthase protein (Hinchee et al., 1988) conferring glyphosate resistance; a nitrilase such as bxn from *Klebsiella ozaenae* which confers resistance to bromoxynil (Stalker et al., 1988); a mutant acetolactate synthase (ALS) which confers resistance to imidazolinone, sulfonylurea or other ALS inhibiting chemicals (European Patent Application 154, 204, 1985); a methotrexate resistant DHFR (Thillet et al., 1988), a dalapon dehalogenase that confers resistance to the herbicide dalapon; or a mutated anthranilate synthase that confers resistance to 5-methyl tryptophan.

An illustrative embodiment of selectable marker capable of being used in systems to select transformants are those that encode the enzyme phosphinothricin acetyltransferase, such as the bar gene from *Streptomyces hygroscopicus* or the pat gene from *Streptomyces viridochromogenes*. The enzyme phosphinothricin acetyl transferase (PAT) inactivates the active ingredient in the herbicide bialaphos, phosphinothricin (PPT). PPT inhibits glutamine synthetase, (Murakami et al., 1986; Twell et al., 1989) causing rapid accumulation of ammonia and cell death.

Screenable markers that may be employed include a β-glucuronidase (GUS) or uidA gene which encodes an enzyme for which various chromogenic substrates are known; an R-locus gene, which encodes a product that regulates the production of anthocyanin pigments (red color) in plant tissues (Dellaporta et al., 1988); a β-lactamase gene (Sutcliffe, 1978), which encodes an enzyme for which various chromogenic substrates are known (e.g., PADAC, a chromogenic cephalosporin); a xylE gene (Zukowsky et al., 1983) which encodes a catechol dioxygenase that can convert chromogenic catechols; an α-amylase gene (Ikuta et al., 1990); a tyrosinase gene (Katz et al., 1983) which encodes an enzyme capable of oxidizing tyrosine to DOPA and dopaquinone which in turn condenses to form the easily-detectable compound melanin; a β-galactosidase gene, which encodes an enzyme for which there are chromogenic substrates; a luciferase (lux) gene (Ow et al., 1986), which allows for bioluminescence detection; an aequorin gene (Prasher et al., 1985) which may be employed in calcium-sensitive bioluminescence detection; or a gene encoding for green fluorescent protein (Sheen et al., 1995; Haseloff et al., 1997; Reichel et al., 1996; Tian et al., 1997; WO 97/41228). The gene that encodes green fluorescent protein (GFP) is also contemplated as a particularly useful reporter gene (Sheen et al., 1995; Haseloff et al., 1997; Reichel et al., 1996; Tian et al., 1997; WO 97/41228). Expression of green fluorescent protein may be visualized in a cell or plant as fluorescence following illumination by particular wavelengths of light.

III. Antisense and Rnai Constructs

Antisense and RNAi treatments represent one way of altering lignin biosynthesis activity in accordance with the invention. In particular, constructs comprising a lignin biosynthesis coding sequence, including fragments thereof, in antisense orientation, or combinations of sense and antisense orientation, may be used to decrease or effectively eliminate the expression of a lignin biosynthesis gene in a plant and obtain an improvement in lignin profile as is described herein. Accordingly, this may be used to "knock-out" the function of a lignin biosynthesis coding sequence or homologous sequences thereof.

Techniques for RNAi are well known in the art and are described in, for example, Lehner et al., (2004) and Downward (2004). The technique is based on the fact that double stranded RNA is capable of directing the degradation of messenger RNA with sequence complementary to one or the other strand (Fire et al., 1998). Therefore, by expression of a particular coding sequence in sense and antisense orientation, either as a fragment or longer portion of the corresponding coding sequence, the expression of that coding sequence can be down-regulated.

Antisense, and in some aspects RNAi, methodology takes advantage of the fact that nucleic acids tend to pair with "complementary" sequences. By complementary, it is meant that polynucleotides are those which are capable of base-pairing according to the standard Watson-Crick complementarity rules. That is, the larger purines will base pair with the smaller pyrimidines to form combinations of guanine paired with cytosine (G:C) and adenine paired with either thymine (A:T) in the case of DNA, or adenine paired with uracil (A:U) in the case of RNA. Inclusion of less common bases such as inosine, 5-methylcytosine, 6-methyladenine, hypoxanthine and others in hybridizing sequences does not interfere with pairing.

Targeting double-stranded (ds) DNA with polynucleotides leads to triple-helix formation; targeting RNA will lead to double-helix formation. Antisense oligonucleotides, when introduced into a target cell, specifically bind to their target polynucleotide and interfere with transcription, RNA processing, transport, translation and/or stability. Antisense and RNAi constructs, or DNA encoding such RNA's, may be employed to inhibit gene transcription or translation or both within a host cell, either in vitro or in vivo, such as within a host plant cell. In certain embodiments of the invention, such an oligonucleotide may comprise any unique portion of a nucleic acid sequence provided herein. In certain embodiments of the invention, such a sequence comprises at least 18, 30, 50, 75 or 100 or more contiguous nucleic acids of the nucleic acid sequence of a lignin biosynthesis gene, and/or complements thereof, which may be in sense and/or antisense orientation. By including sequences in both sense and antisense orientation, increased suppression of the corresponding coding sequence may be achieved.

Constructs may be designed that are complementary to all or part of the promoter and other control regions, exons, introns or even exon-intron boundaries of a gene. It is contemplated that the most effective constructs may include regions complementary to intron/exon splice junctions. Thus, it is proposed that a preferred embodiment includes a construct with complementarity to regions within 50-200 bases of an intron-exon splice junction. It has been observed that some exon sequences can be included in the construct without seriously affecting the target selectivity thereof. The amount of exonic material included will vary depending on the particular exon and intron sequences used. One can readily test whether too much exon DNA is included simply by testing the constructs in vitro to determine whether normal cellular function is affected or whether the expression of related genes having complementary sequences is affected.

As stated above, "complementary" or "antisense" means polynucleotide sequences that are substantially complementary over their entire length and have very few base mismatches. For example, sequences of fifteen bases in length may be termed complementary when they have complementary nucleotides at thirteen or fourteen positions. Naturally, sequences which are completely complementary will be sequences which are entirely complementary throughout their entire length and have no base mismatches. Other sequences with lower degrees of homology also are contemplated. For example, an RNAi or antisense construct which has limited regions of high homology, but also contains a non-homologous region (e.g., ribozyme; see above) could be designed. Methods for selection and design of sequences that generate RNAi are well known in the art (e.g. Reynolds, 2004). These molecules, though having less than 50% homology, would bind to target sequences under appropriate conditions.

It may be advantageous to combine portions of genomic DNA with cDNA or synthetic sequences to generate specific constructs. For example, where an intron is desired in the ultimate construct, a genomic clone will need to be used. The cDNA or a synthesized polynucleotide may provide more convenient restriction sites for the remaining portion of the construct and, therefore, would be used for the rest of the sequence. Constructs useful for generating RNAi may also comprise concatemers of sub-sequences that display gene regulating activity.

IV. Methods for Genetic Transformation

Suitable methods for transformation of plant or other cells for use with the current invention are believed to include virtually any method by which DNA can be introduced into a cell, such as by direct delivery of DNA such as by PEG-mediated transformation of protoplasts (Omirulleh et al., 1993), by desiccation/inhibition-mediated DNA uptake (Potrykus et al., 1985), by electroporation (U.S. Pat. No. 5,384,253, specifically incorporated herein by reference in its entirety), by agitation with silicon carbide fibers (Kaeppler et al., 1990; U.S. Pat. No. 5,302,523, specifically incorporated herein by reference in its entirety; and U.S. Pat. No. 5,464,765, specifically incorporated herein by reference in its entirety), by Agrobacterium-mediated transformation (U.S. Pat. No. 5,591,616 and U.S. Pat. No. 5,563,055; both specifically incorporated herein by reference) and by acceleration of DNA coated particles (U.S. Pat. No. 5,550,318; U.S. Pat. No. 5,538,877; and U.S. Pat. No. 5,538,880; each specifically incorporated herein by reference in its entirety), etc. Through the application of techniques such as these, the cells of virtually any plant species, including biofuel crop species, may be stably transformed, and these cells developed into transgenic plants.

A. *Agrobacterium*-Mediated Transformation

*Agrobacterium*-mediated transfer is a widely applicable system for introducing genes into plant cells because the DNA can be introduced into whole plant tissues, thereby bypassing the need for regeneration of an intact plant from a protoplast. The use of *Agrobacterium*-mediated plant integrating vectors to introduce DNA into plant cells is well known in the art. See, for example, the methods described by Fraley et al., (1985), Rogers et al., (1987) and U.S. Pat. No. 5,563,055, specifically incorporated herein by reference in its entirety.

*Agrobacterium*-mediated transformation is most efficient in dicotyledonous plants and is the preferable method for transformation of dicots, including *Arabidopsis*, tobacco, tomato, alfalfa and potato. Indeed, while *Agrobacterium*-mediated transformation has been routinely used with dicotyledonous plants for a number of years, it has only recently become applicable to monocotyledonous plants. Advances in *Agrobacterium*-mediated transformation techniques have now made the technique applicable to nearly all monocotyledonous plants. For example, *Agrobacterium*-mediated transformation techniques have now been applied to rice (Hiei et al., 1997; U.S. Pat. No. 5,591,616, specifically incorporated herein by reference in its entirety), wheat (McCormac et al., 1998), barley (Tingay et al., 1997; McCormac et al., 1998), alfalfa (Thomas et al., 1990) and maize (Ishidia et al., 1996).

Modern *Agrobacterium* transformation vectors are capable of replication in *E. coli* as well as *Agrobacterium*, allowing for convenient manipulations as described (Klee et al., 1985). Moreover, recent technological advances in vectors for *Agrobacterium*-mediated gene transfer have improved the arrangement of genes and restriction sites in the vectors to facilitate the construction of vectors capable of expressing various polypeptide coding genes. The vectors described (Rogers et al., 1987) have convenient multi-linker regions flanked by a promoter and a polyadenylation site for direct expression of inserted polypeptide coding genes and are suitable for present purposes. In addition, *Agrobacterium* containing both armed and disarmed Ti genes can be used for the transformations. In those plant strains where *Agrobacterium*-mediated transformation is efficient, it is the method of choice because of the facile and defined nature of the gene transfer.

Similarly, *Agrobacterium* mediated transformation has also proven to be effective in switchgrass. Somleva et al. (2002) describe the creation of approximately 600 transgenic switchgrass plants carrying a bar gene and a uidA gene (beta-glucuronidase) under control of a maize ubiquitin promoter and rice actin promoter respectively. Both genes were expressed in the primary transformants and could be inherited and expressed in subsequent generations. Addition of 50 to 200 µM acetosyringone to the inoculation medium increased the frequency of transgenic switchgrass plants recovered.

B. Electroporation

To effect transformation by electroporation, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wounding in a controlled manner. Examples of some species which have been transformed by electroporation of intact cells include maize (U.S. Pat. No. 5,384,253; Rhodes et al., 1995; D'Halluin et al., 1992), wheat (Zhou et al., 1993), tomato (Hou and Lin, 1996), soybean (Christou et al., 1987) and tobacco (Lee et al., 1989).

One also may employ protoplasts for electroporation transformation of plants (Bates, 1994; Lazzeri, 1995). For example, the generation of transgenic soybean plants by electroporation of cotyledon-derived protoplasts is described by Dhir and Widholm in Intl. Patent Appl. Publ. No. WO 9217598 (specifically incorporated herein by reference). Other examples of species for which protoplast transformation has been described include barley (Lazerri, 1995), sorghum (Battraw et al., 1991), maize (Bhattacharjee et al., 1997), wheat (He et al., 1994) and tomato (Tsukada, 1989).

C. Microprojectile Bombardment

Another method for delivering transforming DNA segments to plant cells in accordance with the invention is microprojectile bombardment (U.S. Pat. No. 5,550,318; U.S. Pat. No. 5,538,880; U.S. Pat. No. 5,610,042; and PCT Application WO 94/09699; each of which is specifically incorporated herein by reference in its entirety). In this method, particles may be coated with nucleic acids and delivered into cells by a propelling force. Exemplary particles include those comprised of tungsten, platinum, and preferably, gold. It is contemplated that in some instances DNA precipitation onto metal particles would not be necessary for DNA delivery to a recipient cell using microprojectile bombardment. However, it is contemplated that particles may contain DNA rather than be coated with DNA. Hence, it is proposed that DNA-coated particles may increase the level of DNA delivery via particle bombardment but are not, in and of themselves, necessary.

For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate.

An illustrative embodiment of a method for delivering DNA into plant cells by acceleration is the Biolistics Particle Delivery System, which can be used to propel particles coated with DNA or cells through a screen, such as a stainless steel or Nytex screen, onto a filter surface covered with monocot plant cells cultured in suspension. The screen disperses the particles so that they are not delivered to the recipient cells in large aggregates. Microprojectile bombardment techniques are widely applicable, and may be used to transform virtually any plant species. Examples of species for which have been transformed by microprojectile bombardment include monocot species such as maize (PCT Application WO 95/06128), barley (Ritala et al., 1994; Hensgens et al., 1993), wheat (U.S. Pat. No. 5,563,055, specifically incorporated herein by reference in its entirety), rice (Hensgens et al., 1993), oat (Torbet et al., 1995; Torbet et al., 1998), rye (Hensgens et al., 1993), sugarcane (Bower et al., 1992), and sorghum (Casa et al., 1993; Hagio et al., 1991); as well as a number of dicots including tobacco (Tomes et al., 1990; Buising and Benbow, 1994), soybean (U.S. Pat. No. 5,322,783, specifically incorporated herein by reference in its entirety), sunflower (Knittel et al., 1994), peanut (Singsit et al., 1997), cotton (McCabe and Martinell, 1993), tomato (VanEck et al., 1995), and legumes in general (U.S. Pat. No. 5,563,055, specifically incorporated herein by reference in its entirety).

Richards et al. (2001) describe the creation of transgenic switchgrass plants using particle bombardment. Callus was bombarded with a plasmid carrying a sgfp (green fluorescent protein) gene and a bar (bialaphos and Basta tolerance) gene under control of a rice actin promoter and maize ubiquitin promoter respectively. Plants regenerated from bombarded callus were Basta tolerant and expressed GFP. These primary transformants were then crossed with non-transgenic control plants, and Basta tolerance was observed in progeny plants, demonstrating inheritance of the bar gene.

D. Other Transformation Methods

Transformation of protoplasts can be achieved using methods based on calcium phosphate precipitation, polyethylene glycol treatment, electroporation, and combinations of these treatments (see, e.g., Potrykus et al., 1985; Lorz et al., 1985; Omirulleh et al., 1993; Fromm et al., 1986; Uchimiya et al., 1986; Callis et al., 1987; Marcotte et al., 1988).

Application of these systems to different plant strains depends upon the ability to regenerate that particular plant strain from protoplasts. Illustrative methods for the regeneration of cereals from protoplasts have been described (Toriyama et al., 1986; Yamada et al., 1986; Abdullah et al., 1986; Omirulleh et al., 1993 and U.S. Pat. No. 5,508,184; each specifically incorporated herein by reference in its entirety). Examples of the use of direct uptake transformation of cereal protoplasts include transformation of rice (Ghosh-Biswas et al., 1994), sorghum (Battraw and Hall, 1991), barley (Lazerri, 1995), oat (Zheng and Edwards, 1990) and maize (Omirulleh et al., 1993).

To transform plant strains that cannot be successfully regenerated from protoplasts, other ways to introduce DNA into intact cells or tissues can be utilized. For example, regeneration of cereals from immature embryos or explants can be effected as described (Vasil, 1989). Also, silicon carbide fiber-mediated transformation may be used with or without protoplasting (Kaeppler, 1990; Kaeppler et al., 1992; U.S. Pat. No. 5,563,055, specifically incorporated herein by reference in its entirety). Transformation with this technique is accomplished by agitating silicon carbide fibers together with cells in a DNA solution. DNA passively enters as the cells are punctured. This technique has been used successfully with, for example, the monocot cereals maize (PCT Application WO 95/06128, specifically incorporated herein by reference in its entirety; (Thompson, 1995) and rice (Nagatani, 1997).

E. Tissue Cultures

Tissue cultures may be used in certain transformation techniques for the preparation of cells for transformation and for the regeneration of plants therefrom. Maintenance of tissue cultures requires use of media and controlled environments. "Media" refers to the numerous nutrient mixtures that are used to grow cells in vitro, that is, outside of the intact living organism. The medium usually is a suspension of various categories of ingredients (salts, amino acids, growth regulators, sugars, buffers) that are required for growth of most cell types. However, each specific cell type requires a specific range of ingredient proportions for growth, and an even more specific range of formulas for optimum growth. Rate of cell growth also will vary among cultures initiated with the array of media that permit growth of that cell type.

Nutrient media is prepared as a liquid, but this may be solidified by adding the liquid to materials capable of providing a solid support. Agar is most commonly used for this purpose. BACTOAGAR, GELRITE, and GELGRO are specific types of solid support that are suitable for growth of plant cells in tissue culture.

Some cell types will grow and divide either in liquid suspension or on solid media. As disclosed herein, plant cells will grow in suspension or on solid medium, but regeneration of plants from suspension cultures typically requires transfer from liquid to solid media at some point in development. The type and extent of differentiation of cells in culture will be affected not only by the type of media used and by the environment, for example, pH, but also by whether media is solid or liquid.

Tissue that can be grown in a culture includes meristem cells, Type I, Type II, and Type III callus, immature embryos and gametic cells such as microspores, pollen, sperm and egg cells. Type I, Type II, and Type III callus may be initiated from tissue sources including, but not limited to, immature embryos, seedling apical meristems, root, leaf, microspores and the like. Those cells which are capable of proliferating as callus also are recipient cells for genetic transformation.

Somatic cells are of various types. Embryogenic cells are one example of somatic cells which may be induced to regenerate a plant through embryo formation. Non-embryogenic cells are those which typically will not respond in such a fashion. Certain techniques may be used that enrich recipient cells within a cell population. For example, Type II callus development, followed by manual selection and culture of friable, embryogenic tissue, generally results in an enrichment of cells. Manual selection techniques which can be employed to select target cells may include, e.g., assessing cell morphology and differentiation, or may use various physical or biological means. Cryopreservation also is a possible method of selecting for recipient cells.

Manual selection of recipient cells, e.g., by selecting embryogenic cells from the surface of a Type II callus, is one means that may be used in an attempt to enrich for particular cells prior to culturing (whether cultured on solid media or in suspension).

Where employed, cultured cells may be grown either on solid supports or in the form of liquid suspensions. In either instance, nutrients may be provided to the cells in the form of media, and environmental conditions controlled. There are many types of tissue culture media comprised of various amino acids, salts, sugars, growth regulators and vitamins.

Most of the media employed in the practice of the invention will have some similar components, but may differ in the composition and proportions of their ingredients depending on the particular application envisioned. For example, various cell types usually grow in more than one type of media, but will exhibit different growth rates and different morphologies, depending on the growth media. In some media, cells survive but do not divide. Various types of media suitable for culture of plant cells previously have been described. Examples of these media include, but are not limited to, the N6 medium described by Chu et al. (1975) and MS media (Murashige and Skoog, 1962).

V. Production and Characterization of Stably Transformed Plants

After effecting delivery of exogenous DNA to recipient cells, the next steps generally concern identifying the transformed cells for further culturing and plant regeneration. In order to improve the ability to identify transformants, one may desire to employ a selectable or screenable marker gene with a transformation vector prepared in accordance with the invention. In this case, one would then generally assay the potentially transformed cell population by exposing the cells to a selective agent or agents, or one would screen the cells for the desired marker gene trait.

A. Selection

It is believed that DNA is introduced into only a small percentage of target cells in any one study. In order to provide an efficient system for identification of those cells receiving DNA and integrating it into their genomes one may employ a means for selecting those cells that are stably transformed. One exemplary embodiment of such a method is to introduce into the host cell, a marker gene which confers resistance to some normally inhibitory agent, such as an antibiotic or herbicide. Examples of antibiotics which may be used include the aminoglycoside antibiotics neomycin, kanamycin and paromomycin, or the antibiotic hygromycin. Resistance to the aminoglycoside antibiotics is conferred by aminoglycoside phosphotransferase enzymes such as neomycin phosphotransferase II (NPT II) or NPT I, whereas resistance to hygromycin is conferred by hygromycin phosphotransferase.

Potentially transformed cells then are exposed to the selective agent. In the population of surviving cells will be those cells where, generally, the resistance-conferring gene has been integrated and expressed at sufficient levels to permit cell survival. Cells may be tested further to confirm stable integration of the exogenous DNA.

One herbicide which constitutes a desirable selection agent is the broad spectrum herbicide bialaphos. Bialaphos is a tripeptide antibiotic produced by *Streptomyces hygroscopicus* and is composed of phosphinothricin (PPT), an analogue of L-glutamic acid, and two L-alanine residues. Upon removal of the L-alanine residues by intracellular peptidases, the PPT is released and is a potent inhibitor of glutamine synthetase (GS), a pivotal enzyme involved in ammonia assimilation and nitrogen metabolism (Ogawa et al., 1973). Synthetic PPT, the active ingredient in the herbicide Liberty™ also is effective as a selection agent. Inhibition of GS in plants by PPT causes the rapid accumulation of ammonia and death of the plant cells.

The organism producing bialaphos and other species of the genus *Streptomyces* also synthesizes an enzyme phosphinothricin acetyl transferase (PAT) which is encoded by the bar gene in *Streptomyces hygroscopicus* and the pat gene in *Streptomyces viridochromogenes*. The use of the herbicide resistance gene encoding phosphinothricin acetyl transferase (PAT) is referred to in DE 3642 829 A, wherein the gene is isolated from *Streptomyces viridochromogenes*. In the bacterial source organism, this enzyme acetylates the free amino group of PPT preventing auto-toxicity (Thompson et al., 1987). The bar gene has been cloned (Murakami et al., 1986; Thompson et al., 1987) and expressed in transgenic tobacco, tomato, potato (De Block et al., 1987) *Brassica* (De Block et al., 1989) and maize (U.S. Pat. No. 5,550,318). In previous reports, some transgenic plants which expressed the resistance gene were completely resistant to commercial formulations of PPT and bialaphos in greenhouses.

Another example of a herbicide which is useful for selection of transformed cell lines in the practice of the invention is the broad spectrum herbicide glyphosate. Glyphosate inhibits the action of the enzyme EPSPS which is active in the aromatic amino acid biosynthetic pathway. Inhibition of this enzyme leads to starvation for the amino acids phenylalanine, tyrosine, and tryptophan and secondary metabolites derived thereof. U.S. Pat. No. 4,535,060 describes the isolation of EPSPS mutations which confer glyphosate resistance on the *Salmonella typhimurium* gene for EPSPS, aroA. The EPSPS gene was cloned from *Zea mays* and mutations similar to those found in a glyphosate resistant aroA gene were introduced in vitro. Mutant genes encoding glyphosate resistant EPSPS enzymes are described in, for example, International Patent WO 97/4103. The best characterized mutant EPSPS gene conferring glyphosate resistance comprises amino acid changes at residues 102 and 106, although it is anticipated that other mutations will also be useful (PCT/WO97/4103).

To use the bar-bialaphos or the EPSPS-glyphosate selective system, transformed tissue is cultured for 0-28 days on nonselective medium and subsequently transferred to medium containing from 1-3 mg/l bialaphos or 1-3 mM glyphosate as appropriate. While ranges of 1-3 mg/l bialaphos or 1-3 mM glyphosate will typically be preferred, it is proposed that ranges of 0.1-50 mg/l bialaphos or 0.1-50 mM glyphosate will find utility.

An example of a screenable marker trait is the enzyme luciferase. In the presence of the substrate luciferin, cells expressing luciferase emit light which can be detected on photographic or x-ray film, in a luminometer (or liquid scintillation counter), by devices that enhance night vision, or by a highly light sensitive video camera, such as a photon counting camera. These assays are nondestructive and transformed cells may be cultured further following identification. The photon counting camera is especially valuable as it allows one to identify specific cells or groups of cells which are expressing luciferase and manipulate those in real time. Another screenable marker which may be used in a similar fashion is the gene coding for green fluorescent protein.

B. Regeneration and Seed Production

Cells that survive the exposure to the selective agent, or cells that have been scored positive in a screening assay, may be cultured in media that supports regeneration of plants. In an exemplary embodiment, MS and N6 media may be modified by including further substances such as growth regulators. One such growth regulator is dicamba or 2,4-D. However, other growth regulators may be employed, including NAA, NAA+2,4-D or picloram. Media improvement in these and like ways has been found to facilitate the growth of cells at specific developmental stages. Tissue may be maintained on a basic media with growth regulators until sufficient tissue is available to begin plant regeneration efforts, or following repeated rounds of manual selection, until the morphology of the tissue is suitable for regeneration, at least 2 wk, then transferred to media conducive to maturation of embryoids.

Cultures are transferred every 2 wk on this medium. Shoot development will signal the time to transfer to medium lacking growth regulators.

The transformed cells, identified by selection or screening and cultured in an appropriate medium that supports regeneration, will then be allowed to mature into plants. Developing plantlets are transferred to soiless plant growth mix, and hardened, e.g., in an environmentally controlled chamber, for example, at about 85% relative humidity, 600 ppm $CO_2$, and 25-250 microeinsteins $m^{-2}$ $s^{-1}$ of light. Plants may be matured in a growth chamber or greenhouse. Plants can be regenerated from about 6 wk to 10 months after a transformant is identified, depending on the initial tissue. During regeneration, cells are grown on solid media in tissue culture vessels. Illustrative embodiments of such vessels are petri dishes and Plant Cons. Regenerating plants can be grown at about 19 to 28° C. After the regenerating plants have reached the stage of shoot and root development, they may be transferred to a greenhouse for further growth and testing.

Seeds on transformed plants may occasionally require embryo rescue due to cessation of seed development and premature senescence of plants. To rescue developing embryos, they are excised from surface-disinfected seeds 10-20 days post-pollination and cultured. An embodiment of media used for culture at this stage comprises MS salts, 2% sucrose, and 5.5 µg/l agarose. In embryo rescue, large embryos (defined as greater than 3 mm in length) are germinated directly on an appropriate media. Embryos smaller than that may be cultured for 1 wk on media containing the above ingredients along with $10^{-5}M$ abscisic acid and then transferred to growth regulator-free medium for germination.

C. Characterization

To confirm the presence of the exogenous DNA or "transgene(s)" in the regenerating plants, a variety of assays may be performed. Such assays include, for example, "molecular biological" assays, such as Southern and Northern blotting and PCR™; "biochemical" assays, such as detecting the presence of a protein product, e.g., by immunological means (ELISAs and Western blots) or by enzymatic function; plant part assays, such as leaf or root assays; and also, by analyzing the phenotype of the whole regenerated plant.

D. DNA Integration, RNA Expression and Inheritance

Genomic DNA may be isolated from cell lines or any plant parts to determine the presence of the exogenous gene through the use of techniques well known to those skilled in the art. Note, that intact sequences will not always be present, presumably due to rearrangement or deletion of sequences in the cell. The presence of DNA elements introduced through the methods of this invention may be determined, for example, by polymerase chain reaction (PCR™). Using this technique, discreet fragments of DNA are amplified and detected by gel electrophoresis. This type of analysis permits one to determine whether a gene is present in a stable transformant, but does not prove integration of the introduced gene into the host cell genome. It is typically the case, however, that DNA has been integrated into the genome of all transformants that demonstrate the presence of the gene through PCR™ analysis. In addition, it is not typically possible using PCR™ techniques to determine whether transformants have exogenous genes introduced into different sites in the genome, i.e., whether transformants are of independent origin. It is contemplated that using PCR™ techniques it would be possible to clone fragments of the host genomic DNA adjacent to an introduced gene.

Positive proof of DNA integration into the host genome and the independent identities of transformants may be determined using the technique of Southern hybridization. Using this technique specific DNA sequences that were introduced into the host genome and flanking host DNA sequences can be identified. Hence the Southern hybridization pattern of a given transformant serves as an identifying characteristic of that transformant. In addition it is possible through Southern hybridization to demonstrate the presence of introduced genes in high molecular weight DNA, i.e., confirm that the introduced gene has been integrated into the host cell genome. The technique of Southern hybridization provides information that is obtained using PCR™, e.g., the presence of a gene, but also demonstrates integration into the genome and characterizes each individual transformant.

It is contemplated that using the techniques of dot or slot blot hybridization which are modifications of Southern hybridization techniques one could obtain the same information that is derived from PCR™, e.g., the presence of a gene.

Both PCR™ and Southern hybridization techniques can be used to demonstrate transmission of a transgene to progeny. In most instances the characteristic Southern hybridization pattern for a given transformant will segregate in progeny as one or more Mendelian genes (Spencer et al., 1992) indicating stable inheritance of the transgene.

Whereas DNA analysis techniques may be conducted using DNA isolated from any part of a plant, RNA will only be expressed in particular cells or tissue types and hence it will be necessary to prepare RNA for analysis from these tissues. PCR™ techniques also may be used for detection and quantitation of RNA produced from introduced genes. In this application of PCR™ it is first necessary to reverse transcribe RNA into DNA, using enzymes such as reverse transcriptase, and then through the use of conventional PCR™ techniques amplify the DNA. In most instances PCR™ techniques, while useful, will not demonstrate integrity of the RNA product. Further information about the nature of the RNA product may be obtained by Northern blotting. This technique will demonstrate the presence of an RNA species and give information about the integrity of that RNA. The presence or absence of an RNA species also can be determined using dot or slot blot Northern hybridizations. These techniques are modifications of Northern blotting and will only demonstrate the presence or absence of an RNA species.

E. Gene Expression

While Southern blotting and PCR™ may be used to detect the gene(s) in question, they do not provide information as to whether the corresponding protein is being expressed. Expression may be evaluated by specifically identifying the protein products of the introduced genes or evaluating the phenotypic changes brought about by their expression.

Assays for the production and identification of specific proteins may make use of physical-chemical, structural, functional, or other properties of the proteins. Unique physical-chemical or structural properties allow the proteins to be separated and identified by electrophoretic procedures, such as native or denaturing gel electrophoresis or isoelectric focusing, or by chromatographic techniques such as ion exchange or gel exclusion chromatography. The unique structures of individual proteins offer opportunities for use of specific antibodies to detect their presence in formats such as an ELISA assay. Combinations of approaches may be employed with even greater specificity such as western blotting in which antibodies are used to locate individual gene products that have been separated by electrophoretic techniques. Additional techniques may be employed to absolutely confirm the identity of the product of interest such as evaluation by amino acid sequencing following purification. Although these are among the most commonly employed, other procedures may be additionally used.

Assay procedures also may be used to identify the expression of proteins by their functionality, especially the ability of enzymes to catalyze specific chemical reactions involving specific substrates and products. These reactions may be followed by providing and quantifying the loss of substrates or the generation of products of the reactions by physical or chemical procedures. Examples are as varied as the enzyme to be analyzed and may include assays for PAT enzymatic activity by following production of radiolabeled acetylated phosphinothricin from phosphinothricin and $^{14}$C-acetyl CoA or for anthranilate synthase activity by following loss of fluorescence of anthranilate, to name two.

Very frequently the expression of a gene product is determined by evaluating the phenotypic results of its expression. These assays also may take many forms including but not limited to analyzing changes in the chemical composition, morphology, or physiological properties of the plant. Chemical composition may be altered by expression of genes encoding enzymes or storage proteins which change amino acid composition and may be detected by amino acid analysis, or by enzymes which change starch quantity which may be analyzed by near infrared reflectance spectrometry. Morphological changes may include greater stature or thicker stalks. Most often changes in response of plants or plant parts to imposed treatments are evaluated under carefully controlled conditions termed bioassays.

VI. Breeding Plants of the Invention

In addition to direct transformation of a particular plant genotype with a construct prepared according to the current invention, transgenic plants may be made by crossing a plant having a selected DNA of the invention to a second plant lacking the construct. For example, a selected lignin biosynthesis coding sequence can be introduced into a particular plant variety by crossing, without the need for ever directly transforming a plant of that given variety. Therefore, the current invention not only encompasses a plant directly transformed or regenerated from cells which have been transformed in accordance with the current invention, but also the progeny of such plants.

As used herein the term "progeny" denotes the offspring of any generation of a parent plant prepared in accordance with the instant invention, wherein the progeny comprises a selected DNA construct. "Crossing" a plant to provide a plant line having one or more added transgenes relative to a starting plant line, as disclosed herein, is defined as the techniques that result in a transgene of the invention being introduced into a plant line by crossing a starting line with a donor plant line that comprises a transgene of the invention. To achieve this one could, for example, perform the following steps:

(a) plant seeds of the first (starting line) and second (donor plant line that comprises a transgene of the invention) parent plants;

(b) grow the seeds of the first and second parent plants into plants that bear flowers;

(c) pollinate a flower from the first parent plant with pollen from the second parent plant; and (d) harvest seeds produced on the parent plant bearing the fertilized flower.

Backcrossing is herein defined as the process including the steps of:

(a) crossing a plant of a first genotype containing a desired gene, DNA sequence or element to a plant of a second genotype lacking the desired gene, DNA sequence or element;

(b) selecting one or more progeny plant containing the desired gene, DNA sequence or element;

(c) crossing the progeny plant to a plant of the second genotype; and (d) repeating steps (b) and (c) for the purpose of transferring a desired DNA sequence from a plant of a first genotype to a plant of a second genotype.

Introgression of a DNA element into a plant genotype is defined as the result of the process of backcross conversion. A plant genotype into which a DNA sequence has been introgressed may be referred to as a backcross converted genotype, line, inbred, or hybrid. Similarly a plant genotype lacking the desired DNA sequence may be referred to as an unconverted genotype, line, inbred, or hybrid.

VII. Definitions

Biofuel crop species: A plant that may be used to provide biomass for production of lignocellulosic-derived ethanol. Examples of such plants include switchgrass (*Panicum virgatum*), giant reed (*Arundo donax*), reed canarygrass (*Phalaris arundinacea*), Miscanthus×giganteus, *Miscanthus* sp., sericea lespedeza (*Lespedeza cuneata*), corn, sugarcane, sorghum, millet, ryegrass (*Lolium multiflorum, Lolium* sp.), timothy, Kochia (*Kochia scoparia*), forage soybeans, alfalfa, clover, sunn hemp, kenaf, bahiagrass, bermudagrass, dallisgrass, pangolagrass, big bluestem, indiangrass, fescue (*Festuca* sp.), *Dactylis* sp., *Brachypodium distachyon*, smooth bromegrass, orchardgrass, Kentucky bluegrass, and poplar, among others.

Expression: The combination of intracellular processes, including transcription and translation undergone by a coding DNA molecule such as a structural gene to produce a polypeptide.

Forage crops: Crops including grasses and legumes used as fodder or silage for livestock production.

Genetic Transformation: A process of introducing a DNA sequence or construct (e.g., a vector or expression cassette) into a cell or protoplast in which that exogenous DNA is incorporated into a chromosome or is capable of autonomous replication.

Heterologous: A sequence which is not normally present in a given host genome in the genetic context in which the sequence is currently found In this respect, the sequence may be native to the host genome, but be rearranged with respect to other genetic sequences within the host sequence. For example, a regulatory sequence may be heterologous in that it is linked to a different coding sequence relative to the native regulatory sequence.

Obtaining: When used in conjunction with a transgenic plant cell or transgenic plant, obtaining means either transforming a non-transgenic plant cell or plant to create the transgenic plant cell or plant, or planting transgenic plant seed to produce the transgenic plant cell or plant. Such a transgenic plant seed may be from an $R_0$ transgenic plant or may be from a progeny of any generation thereof that inherits a given transgenic sequence from a starting transgenic parent plant.

Promoter: A recognition site on a DNA sequence or group of DNA sequences that provides an expression control element for a structural gene and to which RNA polymerase specifically binds and initiates RNA synthesis (transcription) of that gene.

$R_0$ transgenic plant: A plant that has been genetically transformed or has been regenerated from a plant cell or cells that have been genetically transformed.

Regeneration: The process of growing a plant from a plant cell (e.g., plant protoplast, callus or explant).

Selected DNA: A DNA segment which one desires to introduce or has introduced into a plant genome by genetic transformation.

Transformation construct: A chimeric DNA molecule which is designed for introduction into a host genome by genetic transformation. Preferred transformation constructs will comprise all of the genetic elements necessary to direct the expression of one or more exogenous genes. In particular embodiments of the instant invention, it may be desirable to introduce a transformation construct into a host cell in the form of an expression cassette.

Transformed cell: A cell the DNA complement of which has been altered by the introduction of an exogenous DNA molecule into that cell.

Transgene: A segment of DNA which has been incorporated into a host genome or is capable of autonomous replication in a host cell and is capable of causing the expression of one or more coding sequences. Exemplary transgenes will provide the host cell, or plants regenerated therefrom, with a novel phenotype relative to the corresponding non-transformed cell or plant. Transgenes may be directly introduced into a plant by genetic transformation, or may be inherited from a plant of any previous generation which was transformed with the DNA segment.

Transgenic plant: A plant or progeny plant of any subsequent generation derived therefrom, wherein the DNA of the plant or progeny thereof contains an introduced exogenous DNA segment not naturally present in a non-transgenic plant of the same strain. The transgenic plant may additionally contain sequences which are native to the plant being transformed, but wherein the "exogenous" gene has been altered in order to alter the level or pattern of expression of the gene, for example, by use of one or more heterologous regulatory or other elements.

Vector: A DNA molecule designed for transformation into a host cell. Some vectors may be capable of replication in a host cell. A plasmid is an exemplary vector, as are expression cassettes isolated therefrom.

VIII. Examples

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

Example 1

Figure 2:
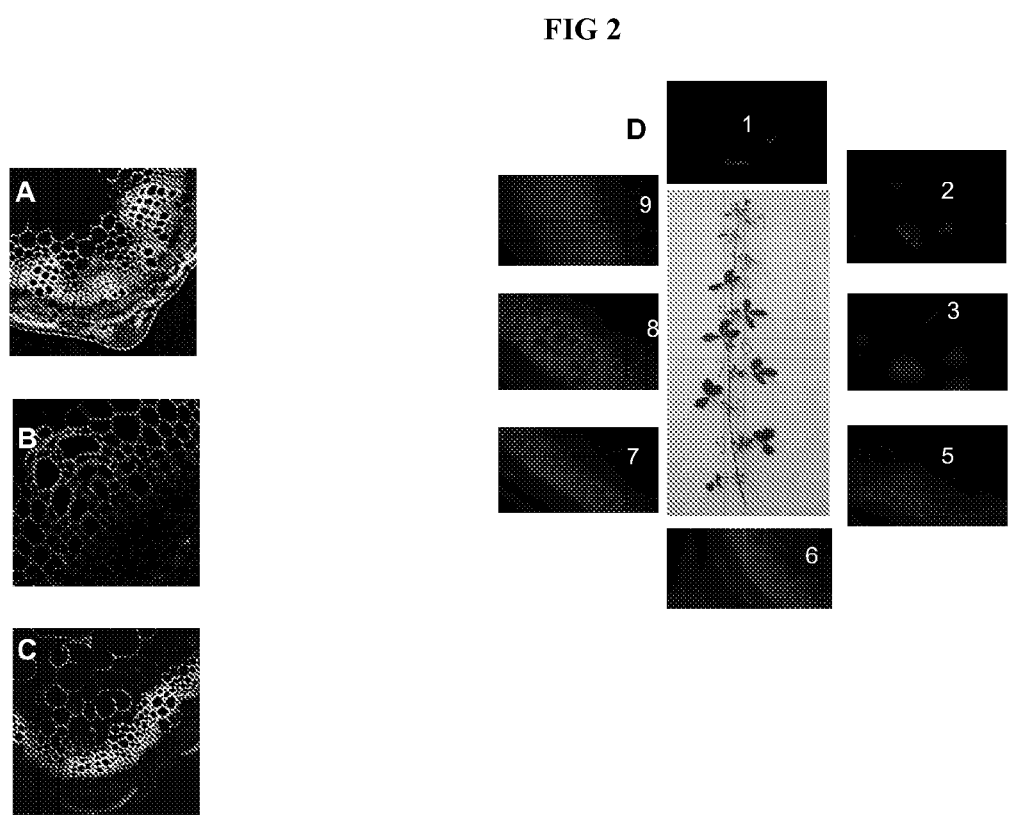
FIG. 2 A-D. UV autofluorescence showing deposition of lignin in the stems of wild-type alfalfa (A); transgenic alfalfa down-regulated in the expression of HCT (B) or COMT (C); (D) Alfalfa stem surrounded by cross sections of individual internodes (numbered 1 at the top to 9 near the base) viewed under UV light. The blue fluorescence indicates the presence of lignin and wall-bound hydroxycinnamic acids.

Effect of Changes in Lignin Content and Composition on Saccharification Efficiency of Pre-Treated and Non Pre-Treated Plant Material Dilute acid pretreatment is an effective and inexpensive technology for pretreatment of lignocellulosic biomass in order to make available for fermentation the carbohydrate content (e.g. sugars of cellulose and hemicellulose) of the biomass. The utilization of both cellulose and hemicellulose in lignocellulosic biomass is essential for the economical production of ethanol. Transgenic alfalfa lines down-regulated in enzymes of the lignin biosynthesis pathway (PAL, C4H, HCT, C3H, CCoaOMT, F5H, COMT) were created previously (e.g. Chen et al., 2006; Reddy et al., 2005; Guo et al., 2001; U.S. Patent Publ. 20040049802), were grown, and biomass was harvested. Microscopic analysis including autofluorescence confirmed significant reductions in cellular lignin deposition in selected transgenic lines (FIG. 2, A-D). Milled transgenic or wild-type alfalfa stems were mixed with dilute $H_2SO_4$ (1% w/w) at a load of 10% (w/w, acid/biomass) and pretreated in an autoclave at 130° C. for 30 min. After pretreatment, the residue and liquid were separated by centrifugation. The liquid (hydrolysate) was stored at −20° C. The treated biomass was washed with hot water, dried, and stored at 4° C. before analysis for lignin and sugar content.

A. Analysis of Lignin Content and Composition from Lines Down-Regulated for Monolignol Synthesis The lignin contents and compositions of treated and untreated alfalfa stems were analyzed using the acetyl bromide ("AcBr"; Fukushima and Hatfield, 2004) and thioacidolysis methods (e.g. Lapierre et al., 1985, 1995), respectively (FIGS. 3A, 3B).

The lignin analysis of stems either acid pre-treated or non pre-treated demonstrated that all of the transgenic lines, which are down-regulated for expression of one of 6 monolignol biosynthetic enzymes (C4H, HCT, C3H, CCoAOMT, F5H, COMT), show less lignin content than controls, except for the F5H down-regulated line (FIGS. 3A, 3B). A progressive reduction of lignin content in both treated and un-treated material was found, in the order: (most lignin) control=F5H>COMT>CCoAOMT≥C4H>C3H>HCT (lowest lignin level). AcBr lignin levels were similar, or higher, in pre-treated materials compared to untreated tissues, and S/G ratio remained constant after pre-treatment, indicating that acid hydrolysis did not remove lignin from cell walls of any of the lines (Table 1). The lignin composition of the various transgenics differed considerably depending on the targeted gene, with S/G ratios varying from about 0.3 to 1.1. The lines with HCT and C3H down-regulated show lower lignin content and a high proportion of H lignin units. C4H, F5H and COMT down-regulated lines show lower levels of S lignin units. The CCoAOMT down-regulated line shows a wild-type level of S lignin units.

TABLE 1

Lignin content and composition in selected transgenic alfalfa lines down-regulated for a lignin biosynthetic gene, C4H, HCT, C3H, CCoAOMT, F5H, COMT. Control: CTR, CK48.

| | Lignin content | | Lignin composition | | | | | | | | | |
|---|---|---|---|---|---|---|---|---|---|---|---|---|
| | Stem | pretreated | | | | | | | | | | |
| | AcBr | AcBr | Stem | | | | | Pretreated | | | | |
| Line | lignin (mg/g) | lignin (mg/g) | H (mmol/g) | G (mmol/g) | S (mmol/g) | Total (mmol/g) | S/G | H (mmol/g) | G (mmol/g) | S (mmol/g) | Total (mmol/g) | S/G |
| CTR1 | 200.7 | 245.5 | 37.2 | 414.8 | 280.9 | 732.9 | 0.68 | 25.4 | 358.5 | 233.1 | 617 | 0.65 |
| CTR2 | 204.5 | 243 | 39.9 | 380.9 | 266.8 | 687.5 | 0.7 | 27.8 | 331.3 | 221.1 | 580.2 | 0.67 |
| CTR3 | 222.3 | 219 | 35.8 | 355.1 | 266.3 | 657.2 | 0.75 | 23.9 | 296.8 | 216.2 | 536.9 | 0.73 |
| CK48 | 200 | 232.9 | 42.6 | 341.4 | 243.7 | 627.6 | 0.68 | 27.2 | 321 | 223.8 | 572 | 0.7 |
| C4H1a | 175.7 | 226.5 | 36.2 | 308.8 | 143.9 | 489 | 0.47 | 24.6 | 281.3 | 132 | 437.8 | 0.47 |
| C4H2b | 126.4 | 170.2 | 37.1 | 228.2 | 61.1 | 326.4 | 0.27 | 17.1 | 188.5 | 48.1 | 253.7 | 0.26 |
| HCT3a | 100.8 | 121.1 | 83.8 | 14.7 | 11.8 | 110.3 | 0.8 | 75.7 | 14 | 11.4 | 101.1 | 0.82 |
| C3H9a | 140.8 | 164.4 | 113.5 | 96.1 | 82.4 | 292.1 | 0.86 | 85.4 | 92.2 | 77 | 254.6 | 0.83 |
| C3H5a | 140.3 | 177 | 132.6 | 99.1 | 76.1 | 307.8 | 0.77 | 41.6 | 29 | 20.4 | 91 | 0.7 |
| C3H4a | 125.9 | 177.4 | 141.1 | 46.4 | 37.3 | 224.9 | 0.8 | 92.7 | 36.5 | 29.4 | 158.6 | 0.8 |
| CCoAOMT305 | 155.2 | 204.2 | 30.8 | 192.3 | 205.8 | 428.9 | 1.07 | 29.8 | 197.9 | 203 | 430.6 | 1.03 |
| CCoAOMT315 | 160.9 | 185.6 | 47.6 | 243.1 | 248.8 | 539.6 | 1.02 | 28.9 | 194.2 | 191.8 | 414.9 | 0.99 |
| F5H4a | 226.7 | 223.5 | 32.4 | 356.6 | 118.4 | 507.4 | 0.33 | 25.1 | 365.8 | 122.5 | 513.3 | 0.33 |
| F5H1a | 215.8 | 258.2 | 31.6 | 399.9 | 107.4 | 538.9 | 0.27 | 22.6 | 392.2 | 106.7 | 521.4 | 0.27 |
| COMT310 | 163.7 | 207.2 | 35.2 | 267.4 | 100.9 | 403.5 | 0.38 | 24.3 | 241.4 | 94.6 | 360.4 | 0.39 |
| COMT5 | 177.7 | 220.3 | 37.2 | 307.2 | 149.9 | 494.3 | 0.49 | 25.8 | 278.7 | 138.7 | 443.3 | 0.5 |

B. Sugar Content and Composition of Lignocellulosic Biomass and Hydrolysates

To determine the sugar contents and compositions of treated and untreated stems, approximately 0.35 g samples were weighed into glass centrifuge tubes. Exactly 3 ml of 72% sulfuric acid was added and the tubes were placed in a 30° C. water bath for one hour. The contents of the tubes were then washed into a 250 ml beaker with 84 ml of water and the beakers were placed in an autoclave at 130° C. for 1 hour. The total sugar contents in the solutions were determined by the phenol sulfuric acid assay. The sugar contents of hydrolysates were also determined by the phenol-sulfuric acid method (Dubois et al., 1956). Sugar compositions of hydrolyzates were determined by GC/MS of the alditol acetate derivatives. Compared to the wild type control, all the transgenic lines have higher carbohydrate yields, except for the F5H down-regulated line following cellulase digestion (Table 2).

TABLE 2

Total sugar released from cell walls of control alfalfa plants, and plants with reduced lignin levels and altered lignin composition resulting from antisense down-regulation of the enzymes indicated. Untreated and pre-treated biomass was incubated with a mixture of excess Celluclast 1.5 L and Novozyme 188 for the times shown:

| | Total sugar released by cellulase (% of cell wall residue) | | | |
|---|---|---|---|---|
| Line | Untreated 48 h | Untreated 72 h | Pre-treated 48 h | Pre-treated 72 h |
| Control (n = 4) | 15.2 ± 2.9 | 15.5 ± 1.1 | 27.4 ± 1.8 | 29.1 ± 2.1 |
| C4H (n = 2) | 24.9 ± 5.6 | 25.5 ± 6.6 | 42.5 ± 7.5 | 43.9 ± 7.7 |
| HCT3a | 44.4 | 49.5 | 57.4 | 63.1 |
| C3H (n = 3) | 33.0 ± 5.2 | 37.7 ± 3.6 | 46.2 ± 5.1 | 52.2 ± 5.5 |
| CCoAOMT (n = 2) | 15.9 ± 0.9 | 17.9 ± 0.8 | 41.7 ± 1.3 | 43.7 ± 0.7 |
| F5H (n = 2) | 14.1 ± 0.6 | 14.9 ± 0.2 | 26.7 ± 0.8 | 28.3 ± 0.7 |
| COMT(n = 2) | 21.0 ± 2.8 | 23.1 ± 1.6 | 37.5 ± 1.1 | 41.5 ± 3.5 |

Figure 4:
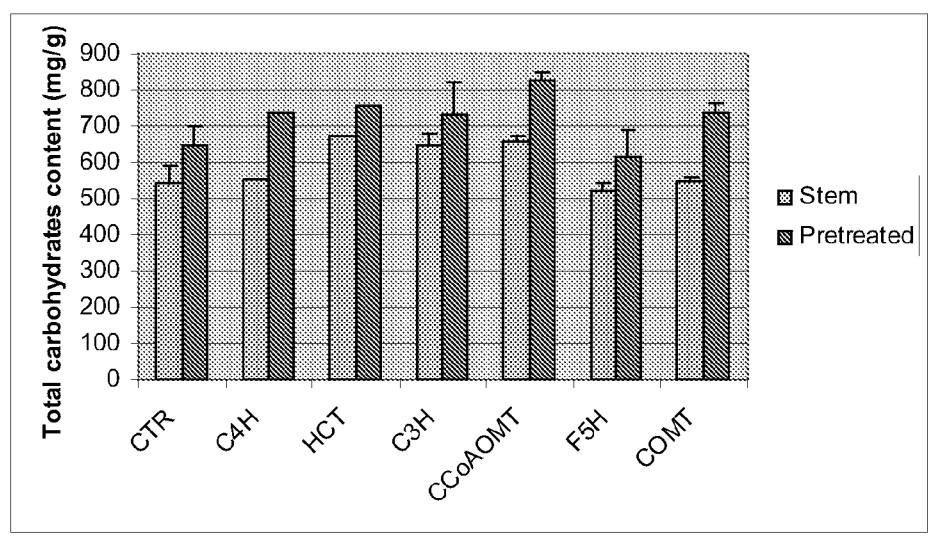
FIG. 4. Comparison of carbohydrate content in stems from control and lignin-modified transgenic lines with or without dilute acid hydrolysis pre-treatment.
Figure 7A:
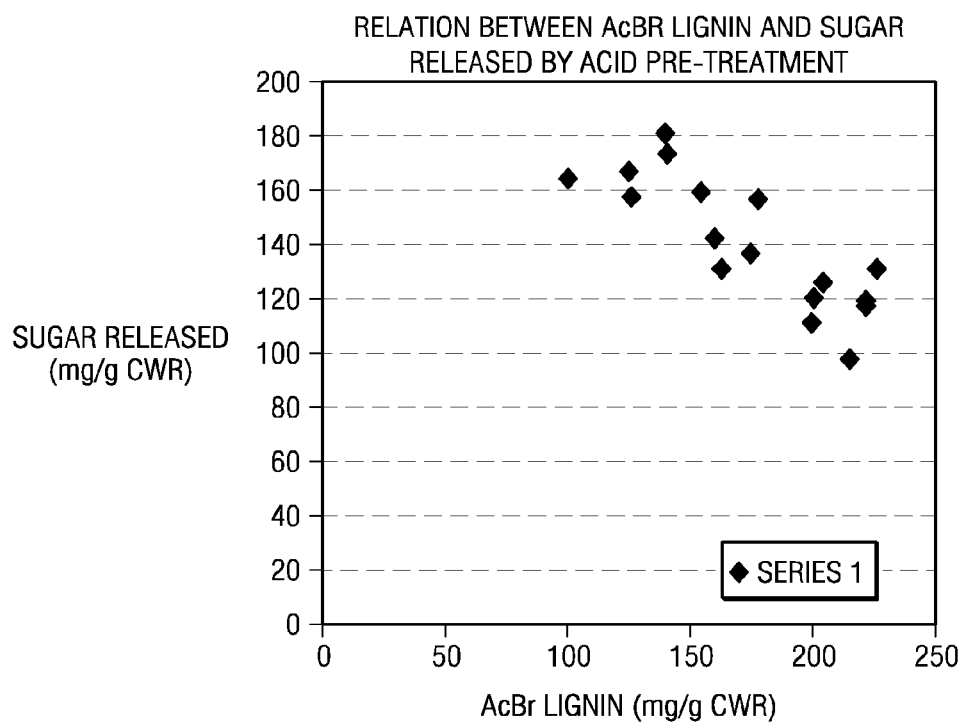
FIG. 7. Relationships between lignin levels/properties and saccharification potential for biomass derived from a series of alfalfa lines with altered lignin content and composition as a result of targeting six enzymes in the monolignol pathway for antisense down-regulation. Each point represents an individual control or transgenic plant. (A) Sugar released by sulfuric acid pre-treatment as a function of lignin content. (B) Sugar released by sulfuric acid pre-treatment as a function of lignin composition. (C) Sugar released from pre-treated biomass by enzymatic digestion as a function of lignin content. (D) Sugar released from pre-treated biomass by enzymatic digestion as a function of lignin composition.
Figure 7B:
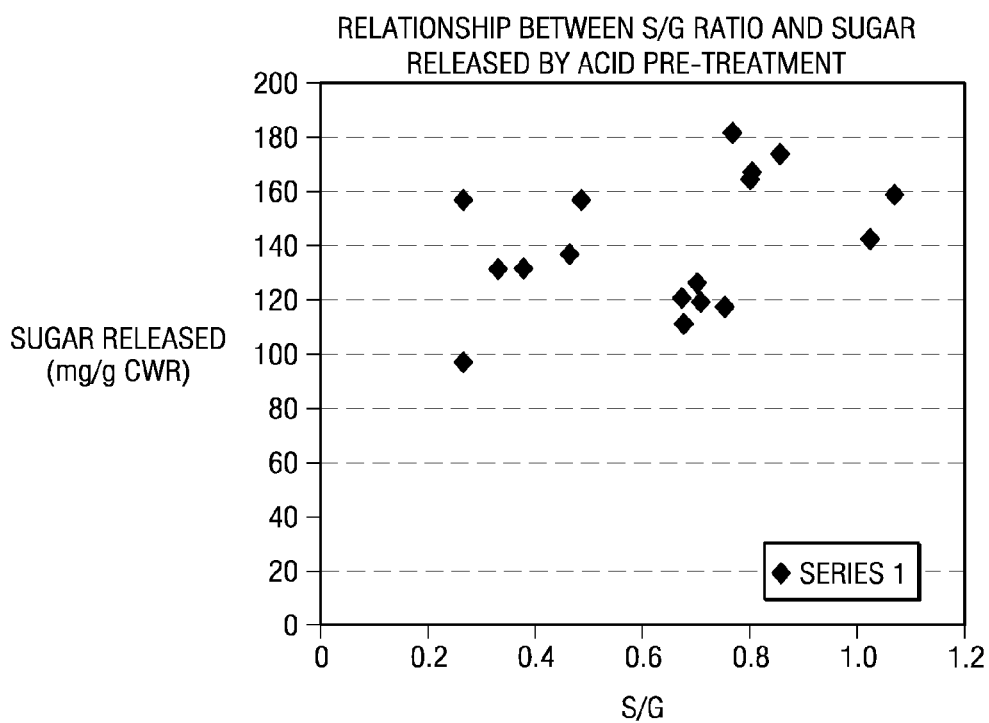

Plants with the greatest reduction in lignin levels had the highest total carbohydrate levels in biomass prior to treatment, as measured by the phenol-sulfuric acid method (Table 3). This partly reflects compensation for the reduction in lignin level when results are expressed as a % of total cell wall material, but may also indicate improved accessibility to the phenol sulfuric acid reagent. Carbohydrate content of stem tissue is shown in FIG. 4. The amount of carbohydrate released by acid pre-treatment increased with decreasing lignin content (FIG. 7A), with the highest value (a 51% increase compared to controls) in one of the C3H down-regulated lines. Individual sugars present in the acid hydrolysates were analyzed by GC/MS, and comprised, in order of abundance, xylose, arabinose, glucose and galactose (FIG. 5B). Reduction of lignin content therefore leads to increased efficiency of acid pre-treatment for solubilization of hemicellulosic cell wall polymers. However, there was no significant relationship between lignin composition and sugar release by acid pre-treatment (FIG. 7B).

Figure 5C:
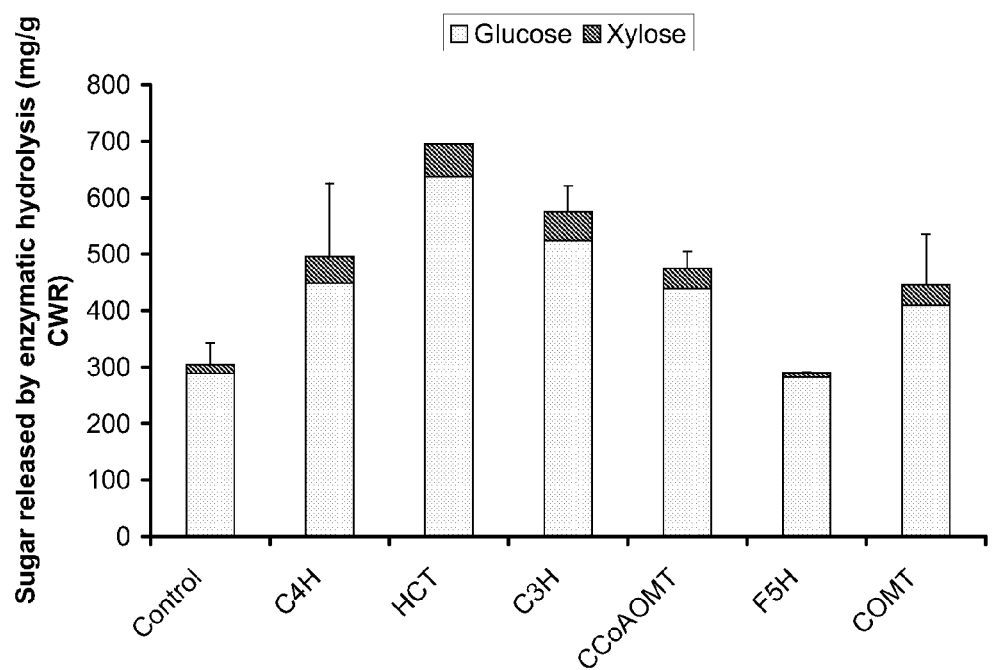
Figure 7C:
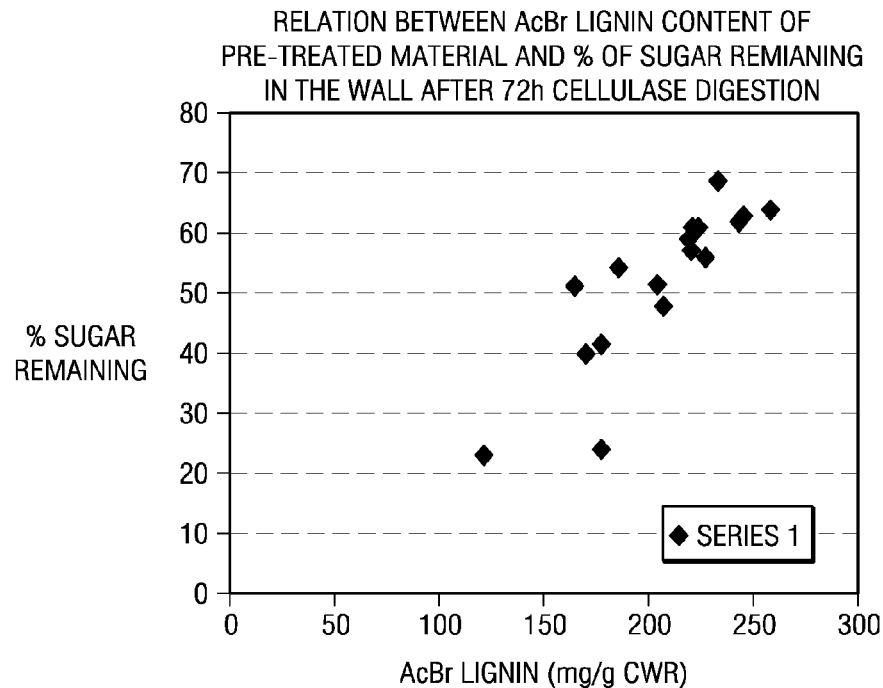
Figure 7D:
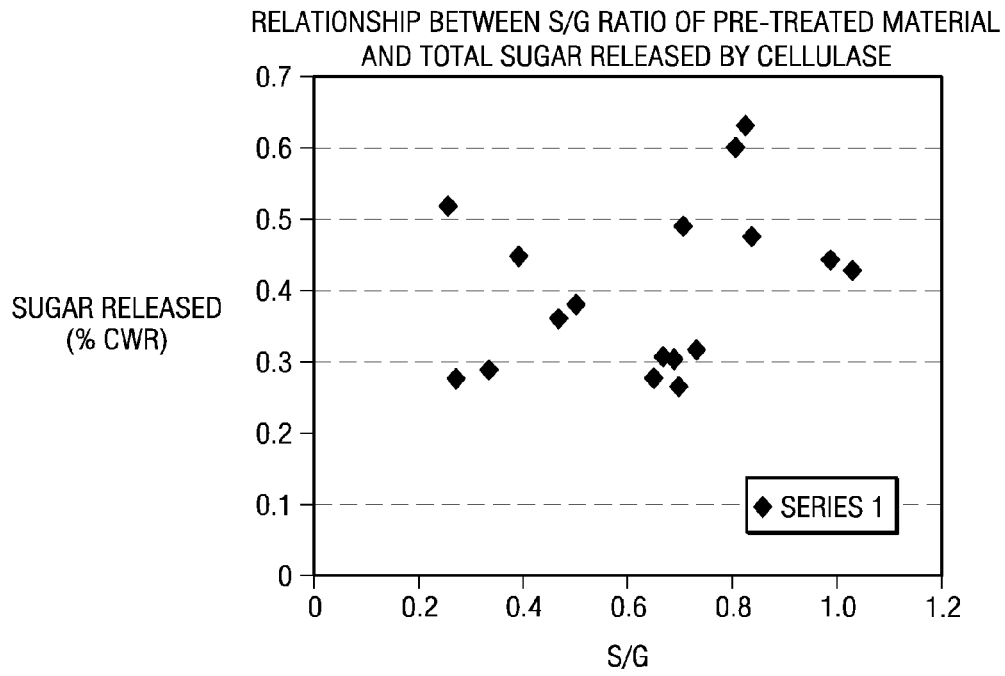

Acid pre-treated biomass was washed and incubated with a cellulase/cellobiase mixture. Incubation for 72 h released little additional sugar from that released after 48 h. However, striking differences were observed in the levels of total sugar released from cell walls of the various lines (Table 2, Table 3, FIG. 7C). Between 59-69% of the total sugar in the pre-treated walls of control lines remained insoluble after cellulase treatment, whereas this value was only 23% in HCT3a and one of the three C3H lines (FIG. 7C). HPLC analysis of the released sugars revealed primarily glucose, with a smaller amount of xylose (FIG. 5C). Thus, reduction of lignin content leads to a striking increase in efficiency of enzymatic hydrolysis of cellulosic cell wall polymers, and this is inversely related to lignin content (FIG. 7). There was no significant overall relationship between lignin composition and the amount of sugar released by cellulase (FIG. 7D). However, CCoAOMT down-regulated material (with the highest S/G ratio; Table 1) exhibited increased saccharification after, but not before, pre-treatment, unlike biomass from non-pre-treated C4H-, HCT-, C3H- and COMT-down-regulated lines, which yielded more sugar than pre-treated control material (Table 2). This suggests that differences in lignin composition and/or structure can affect the amenability of cell walls to acid pre-treatment, and is consistent with the previous observation that reduced S/G ratio favors acid saccharification in hybrid poplar (Davison et al., 2006) since the increased S/G ratio in the CCoAOMT lines (Table 1) appears to negate the positive effect of reduced lignin content on sugar yield from acid pre-treatment. These results contrast with the benefit of a high S/G ratio for efficient paper pulping in trees (e.g. Pilat, 2002).

Thus changes in lignin composition for improving saccharification efficiency do not necessarily correlate with changes for improved paper pulping efficiency or forage digestibility.

By-passing pre-treatment therefore has advantages beyond process simplification. Third, with the exception of the CCoAOMT results, the data suggest that lignin composition per se is not an important factor for efficiency of enzymatic saccharification. This is consistent with the impact of lignin content rather than composition on digestibility of alfalfa in fistulated steers (Reddy et al., 2005). In the present work, different lignin compositions were obtained over a range of different lignin contents—the lack of effect of lignin compo-

TABLE 3

Total sugar released from cell walls following cellulase treatment of 48-72 hours, in absence or presence of acid pre-treatment

| | Total sugar (mg/g CWR) | | | Total sugar (% of CWR) | | | | Total sugar (% of total sugar in sample) | | | |
|---|---|---|---|---|---|---|---|---|---|---|---|
| | Untreated | Pretreated | Hydrolysate | Untreated | | Pretreated | | Untreated | | Pretreated | |
| Line | total | total | total | 48 h | 72 h | 48 h | 72 h | 48 h | 72 h | 48 h | 72 h |
| CTR1 | 621 | 676.7 | 120.7 | 17.3 | 16.9 | 27 | 27.6 | 25.5 | 24.9 | 39 | 36.5 |
| CTR2 | 586.2 | 656.2 | 126.1 | 12.3 | 14.1 | 27 | 30.7 | 17.9 | 20.6 | 37.5 | 38.3 |
| CTR3 | 641.9 | 650.9 | 117.6 | 18.7 | 16.2 | 30.3 | 31.4 | 27 | 23.3 | 44 | 41 |
| CK48 | 597.5 | 734.7 | 111.1 | 12.4 | 14.7 | 25.4 | 26.5 | 18.5 | 21.9 | 33.6 | 31.4 |
| C4H1a | 620 | 765 | 137.1 | 14.9 | 18.8 | 35 | 36.2 | 27.2 | 26.6 | 47.4 | 44.1 |
| C4H2b | 643.2 | 757.3 | 157.6 | 30.4 | 32 | 50 | 51.6 | 41.3 | 43.5 | 64.5 | 60 |
| HCT3a | 731.9 | 747.6 | 164.3 | 44.4 | 49.5 | 57.4 | 63.1 | 56.3 | 62.7 | 78 | 77.1 |
| C3H9a | 672.6 | 827.7 | 173.2 | 29.6 | 34.2 | 41.9 | 47.4 | 40.8 | 47.1 | 48.3 | 49.3 |
| C3H5a | 699 | 767.4 | 180.8 | 29.6 | 36.3 | 43.3 | 49.4 | 40.5 | 50.7 | 57.1 | 58.6 |
| C3H4a | 683.1 | 666.1 | 167 | 40.4 | 42.7 | 53.4 | 59.9 | 55.1 | 58.3 | 75.5 | 76.3 |
| CCoAOMT305 | 674.5 | 797.1 | 159.1 | 15 | 17.1 | 40.4 | 43 | 22.1 | 25.2 | 51.7 | 49.4 |
| CCoAOMT315 | 684 | 858.8 | 141.6 | 15 | 18.7 | 42.9 | 44.4 | 23.3 | 26 | 49 | 45.7 |
| F5H4a | 604.6 | 611.1 | 131.4 | 14.7 | 15.1 | 27.4 | 29 | 21.9 | 22.4 | 41.3 | 39.5 |
| F5H1a | 589.9 | 678.9 | 98 | 13.4 | 14.7 | 25.9 | 27.6 | 19.9 | 21.7 | 37.6 | 36.1 |
| COMT310 | 633.6 | 751.6 | 130.8 | 23.7 | 24.7 | 38.5 | 45 | 33.2 | 34.7 | 49.2 | 51.8 |
| COMT5 | 631.2 | 772.2 | 157.2 | 18.2 | 21.5 | 36.4 | 38 | 25.2 | 29.7 | 46.1 | 43.3 |

Figure 6:
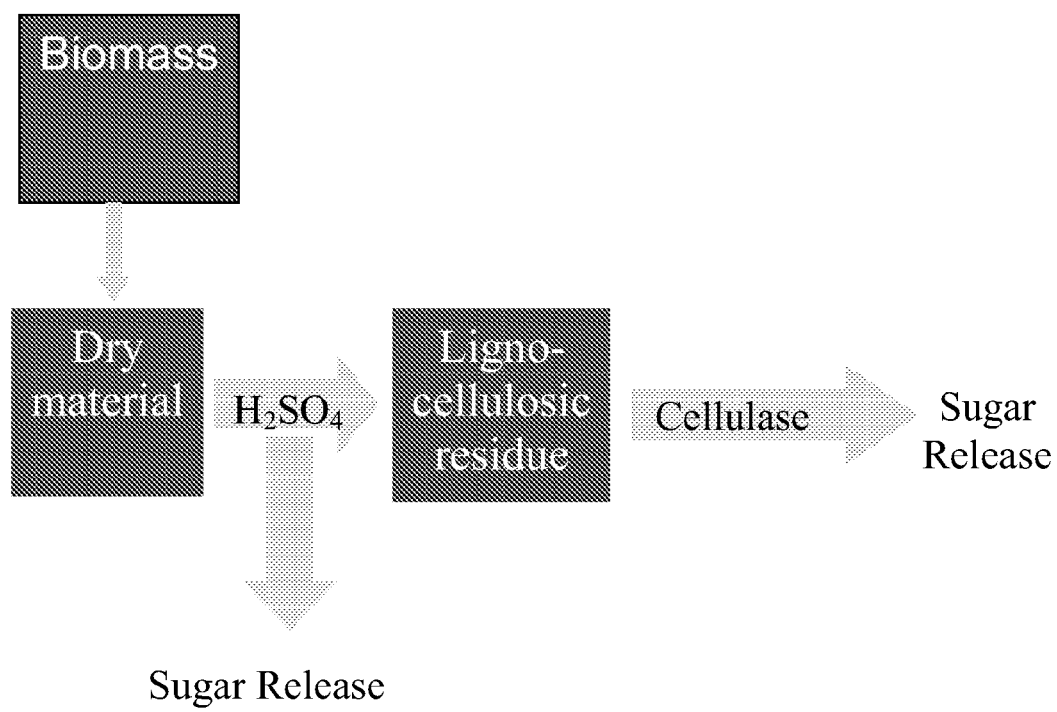
FIG. 6. Exemplary processing scheme for saccharification of lignocellosic biomass.

All of the transgenic lines were found to exhibit significantly improved sugar yields after dilute acid hydrolysis. Total sugar content of hydrolysates (mg/g) was from 116% to 142% of control values in five out of the six lines (FIG. 5A). Total monosaccharide content also increased in most lines (FIG. 5B). This indicated that an enhanced yield of fermentable sugars may be obtained from transgenic lignin-reduced plants using conventional dilute acid pretreatment at a moderate temperature. Such treatments could include, for instance and as described in Example 1, dilute $H_2SO_4$ (e.g. 0.3%-2.0% w/w, at a load of about 10% (w/w, acid/biomass)) and pretreated in an autoclave at 130° C.±20° C. Most of the sugars in the hydrolysate come from hemicellulose. The improved hydrolysis of hemicellulose in the transgenic plant material is expected to open the structure of the residual cellulosic fraction for enhanced enzymatic hydrolysis in a second stage (cellulose digestion) of the bioethanol production process (e.g. FIG. 6).

The above results identify lignin as likely being the major factor in recalcitrance of cell walls, particularly to enzymatic hydrolysis. Second, the results indicate that removal of lignin can obviate the need for the acid pre-treatment step, because more sugar is released by enzymatic hydrolysis of untreated cell walls of the HCT and C3H transgenics than from pretreated cell walls of control plants (Table 2).

Further, acid hydrolysis of the hemicellulosic fraction produces acids and furfural derivatives that are inhibitory to the later fermentation step and therefore reduce ethanol yields (Badger, 2002; Haemelinck et al., 2005), and the harsh chemical pre-treatment makes it impossible to take advantage of in planta expression of cellulases to increase the efficiency of the enzymatic processing step (e.g. Sticklen et al., 2006).

sition on enzymatic hydrolysis was, however, clearly apparent when only lines with similar lignin content, but altered composition, were compared (e.g. FIGS. 7B, 7D). With lignin content now identified as a major impediment to saccharification by both acid pre-treatment and enzymatic hydrolysis in alfalfa, the benefits of similar approaches were indicated for lignin modification and improvement in processing efficiency in bioenergy crops such as poplar, switchgrass and *Miscanthus*.

Example 2

Effects of Lignin Modulation on Biomass Yield

Figure 8:
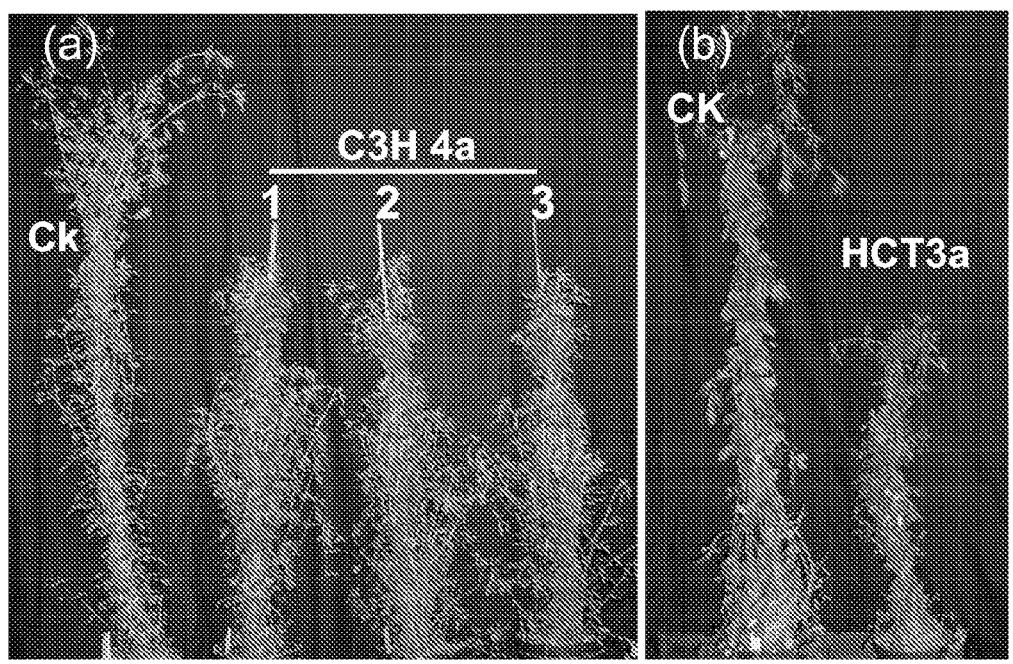
FIG. 8. Morphology of C3H and HCT down-regulated alfalfa, and effect on biomass yield. (A) C3H lines compared to control non-transgenic line (Ck). (B) HCT down-regulated line compared to control (CK).

Transgenic alfalfa plants down-regulated in expression of COMT or CCoAOMT have similar biomass yields to control plants (Guo et al., 2001), whereas strongly down-regulating C3H or HCT results in a reduction in overall biomass accompanied, in HCT transgenics, by increased branching (e.g. Reddy et al., 2005) (FIG. 8). The HCT3a line had the lowest biomass at flowering among the materials analyzed here. Biomass (dry weight) reductions of from 18-40% in a series of HCT transgenics including plants with greater lignin reduction than displayed by HCT3a were previously shown (Shadle 2006). A 166% increase in enzymatic hydrolysis efficiency would be required to offset a 40% reduction in overall biomass yield. The increased enzymatic hydrolysis efficiency of approximately 217% in HCT3a therefore reflects a considerable improvement in fermentable glucose production on a per plant basis, even with reduced biomass yield. In the case of the two COMT down-regulated lines studied, the increased yields of sugars from hemicellulosic (9-32%) and cellulosic polymers (31-55%) represent direct gains in saccharification efficiency in the absence of biomass yield reduction.

Example 3

Modulation of Monolignol Biosynthesis in Transgenic Grass Plants

Transgenic grass lines, such as switchgrass, are created which are down-regulated in each of seven enzymes in the monolignol biosynthetic pathway (e.g. FIG. 1). These enzymes are the three cytochrome P450 enzymes of the lignin pathway (cinnamate 4-hydroxylase (C4H); coumarate 3-hydroxylase (C3H); ferulate 5-hydroxylase (F5H)); two O-methyltransferases (COMT and CCoAOMT), as well as L-phenylalanine ammonia-lyase (PAL) and hydroxycinnamoyl CoA: quinate/shikimate hydroxycinnamoyl transferase (HCT). Additional non-limiting targets for down-regulation in order to modify lignin biosynthesis may include aldehyde dehydrogenase (ALDH), monolignol-lignin-specific glycosyltransferase(s), and cinnamyl alcohol dehydrogenase (CAD). Exemplary nucleic acid sequences coding for such enzymes or portions of such enzymes include those from bermudagrass, switchgrass, and tall fescue, such as: bermuda grass C3H (SEQ ID NO:1) and CCOMT (SEQ ID NO:2); switchgrass ALDH (SEQ ID NO:3), CAD (SEQ ID NO:4), HCT (SEQ ID NO:10), and COMT (SEQ ID NO:5); and tall fescue C4H (SEQ ID NO:6), CAD (SEQ ID NO:7); CCOMT (SEQ ID NO:8), and COMT (SEQ ID NO:9; GenBank Accession AF153824). These sequences, or fragments or portions thereof, may be used to alter expression of a target gene, or may be used according to methods well known in the art to isolate homologous sequence(s) from lignocellulosic biomass crop species of interest which may themselves be used to down-regulate lignin synthesis in a plant of interest. Such sequences may be obtained, for instance, by RT-PCR with primers designed based on bermuda grass, switchgrass, tall fescue, or other grass species EST information.

A. Down-Regulation of Phenylalanine Ammonia-Lyase (PAL) in Transgenic Switchgrass PAL is the first enzyme in the lignin biosynthetic pathway. In *P. virgatum* a sequence corresponding to the PAL gene is identified and selected for antisense mediated down-regulation of PAL. Switchgrass tissue is transformed with selected sequence(s), and PAL-down-regulated lines are obtained.

B. Down-Regulation of Cinnamate 4-Hydroxylase (C4H) in Transgenic Switchgrass

Transgenic lines are screened and independent lines are obtained containing C4H sequence(s) in the antisense orientation under the control of a plant expressible promoter, that are down regulated for C4H. The lignin composition of these down-regulated lines shows a decrease in the syringyl/guaiacyl monomer ratio, and also a decrease in the total lignin compared to control lines.

C. Down-Regulation of Hydroxycinnamoyl CoA: Quinate/Shikimate Hydroxycinnamoyl Transferase (HCT) in Transgenic Switchgrass Transgenic lines comprising an antisense hydroxycinnamoyl transferase (HCT) from switchgrass are screened, and a HCT-down-regulated line is identified.

D. Down-Regulation of 4-Coumarate 3-Hydroxylase (C3H) in Transgenic Switchgrass

A switchgrass stem cDNA library is screened to isolate sequences encoding C3H, and a sequence is cloned in antisense orientation for introduction to switchgrass. Following introduction of C3H sequences into switchgrass, transgenic lines are screened yielding a C3H-down-regulated line.

E. Down-Regulation of Caffeoyl Coenzyme A O-Methyltransferase (CCoAOMT) in Transgenic Switchgrass CCoAOMT sequences are isolated by screening a switchgrass stem cDNA library as above, and cloned in antisense orientation for introduction to switchgrass. Transgenic lines are screened, yielding a CCoAOMT-down-regulated line.

F. Down-Regulation of Ferulate 5-Hydroxylase (F5H) in Transgenic Switchgrass

F5H sequences from switchgrass are isolated by screening a switchgrass stem cDNA library and cloned in antisense orientation for introduction to switchgrass. A transgenic F5H-down-regulated line is identified.

G. Down-Regulation of Caffeic Acid O-Methyltransferase (COMT) in Transgenic Switchgrass Sequences encoding switchgrass COMT are isolated (e.g. SEQ ID NO:5) by screening a switchgrass stem cDNA library, and cloned in antisense orientation for introduction to switchgrass. Transgenic COMT-down-regulated lines are identified.

Example 4

Fermentability of Lignin-Modified Switchgrass and Relationship with Lignin Content and Composition In vitro and in situ studies are performed to assess changes in availability of fermentable carbohydrates (e.g. xylose, glucose) in biomass of transgenic switchgrass derived from transgenic lines exhibiting down-regulation of lignin biosynthetic enzymes, in conjunction with acid and/or enzymatic treatment of the biomass. The procedures in Examples 1-3 are used.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The references listed below are incorporated herein by reference to the extent that they supplement, explain, provide a background for, or teach methodology, techniques, and/or compositions employed herein.

U.S. Pat. No. 3,990,994; U.S. Pat. No. 4,461,648; U.S. Pat. No. 4,535,060; U.S. Pat. No. 4,600,590; U.S. Pat. No. 5,000,000; U.S. Pat. No. 5,037,663; U.S. Pat. No. 5,302, 523; U.S. Pat. No. 5,322,783; U.S. Pat. No. 5,384,253; U.S. Pat. No. 5,451,514; U.S. Pat. No. 5,464,765; U.S. Pat. No. 5,508,184; U.S. Pat. No. 5,538,877; U.S. Pat. No. 5,538, 880; U.S. Pat. No. 5,545,818; U.S. Pat. No. 5,550,318; U.S. Pat. No. 5,563,055; U.S. Pat. No. 5,591,616; U.S. Pat. No.

5,610,042; U.S. Pat. No. 5,850,020; U.S. Pat. No. 5,922,928; U.S. Pat. No. 5,972,118; U.S. Pat. No. 6,610,908; U.S. Pat. No. 6,841,721.
U.S. Pat. Publ 20030005481; U.S. Pat. Publ 20040049802
Abdullah et al., *Biotechnology*, 4:1087, 1986.
Bailey and Elkan, pp. 28-36 in: *Proceedings of the Second International Conference on Intelligent Systems for Molecular Biology*, AAAI Press, Menlo Park, Calif., 1994.
Bailey and Gribskov, *Bioinformatics*, Vol. 14, pp. 48-54, 1998. Badger, pp. 17-21 in *Trends in new crops and new uses* J. Janick, A. Whipkey, Eds., ASHS Press, Alexandria, Va., 2002.
Bates, *Mol. Biotechnol.*, 2(2):135-145, 1994.
Battraw and Hall, *Theor. App. Genet.*, 82(2):161-168, 1991.
Baucher, et al., *Plant Mol Biol* 39:437-447, 1999.
Baucher et al., *Crit. Rev. Biochem Mol. Biol.*, 38:305-350, 2003.
Bevan et al., *Nucleic Acids Research*, 11(2):369-385, 1983.
Bhattacharjee et al., *J. Plant Bioch. and Biotech.* 6, (2):69-73. 1997.
Blancaflor et al., *Planta*, 217(2):206-17, 2003.
Bouchez et al., *EMBO Journal*, 8(13):4197-4204, 1989.
Boudet, et al., *New Phytol.* 129:203-236, 1995.
Bower et al., *Plant Journal*, 2:409-416. 1992.
Buckley et al., *Eur. J. Pharmacol.*, 396:141-149, 2000.
Buising and Benbow, *Mol Gen Genet*, 243(1):71-81. 1994.
Buxton and Russell, 1988. *Crop Sci* 28:553-558.
Callis et al., *Genes Dev.*, 1:1183-1200, 1987.
Casa et al., *Proc. Natl. Acad. Sci. USA*, 90(23):11212-11216, 1993.
Casler, M. D. *Crop Sci* 27:931-934, 1987.
Chandler et al., *The Plant Cell*, 1:1175-1183, 1989.
Chapman et al., *Plant Physiol.*, 120:1157-1164, 1999.
Chapman et al., *Plant. Physiol* 116: 1163-1168, 1998.
Chapman, *Chem. Phys. Lipids*, 108:221-230, 2000.
Chen et al., *Plant J.* 48:113-124, 2006.
Christou; et al., *Proc. Natl. Acad. Sci. USA*, 84:3962-3966, 1987.
Chu et al., *Scientia Sinica*, 18:659-668, 1975.
Conkling et al., *Plant Physiol.*, 93:1203-1211, 1990.
DE App. 3642,829
Davin and Lewis, *Rec Adv Phytochem.* 26:325-375, 1992.
Davison et al., *Appl. Biochem. Biotechnol.* 129-132: 427-435, 2006.
De Block et al., *EMBO Journal*, 6(9):2513-2518, 1987.
De Block et al., *Plant Physiol.*, 91:694-701, 1989.
De Petrocellis et al., *Chemistry and Physics of Lipids* 108: 191-209, 2000
Dellaporta et al., *In: Chromosome Structure and Function: Impact of New Concepts*, 18th Stadler Genetics Symposium, 11:263-282, 1988.
Devane et al., *Science* 258: 1946-1949, 1992
D'Halluin et al., *Plant Cell*, 4(12):1495-1505, 1992.
Dixon, et al., *Rec Adv Phytochem.*, 28:153-178, 1994.
Di Marzo et al., *Nature* 372: 686-691, 1994
Downward, *BMJ*, 328(7450):1245-1248, 2004.
Dubois, et al., *Anal. Chem.* 28:250, 1956.
Duff and Murray, *Bioresource Tech.*, 55:1-33, 1995.
EP Patent Applic. 154,204
Ebert et al., 84:5745-5749, *Proc. Natl. Acad. Sci. USA*, 1987.
Ellis et al., *EMBO Journal*, 6(11):3203-3208, 1987.
Fire et al., *Nature*, 391: 806-11, 1998.
Fraley et al., *Bio/Technology*, 3:629-635, 1985.
Franke et al., *Plant J.* 30:33-45 (2002).
Fromm et al., *Nature*, 319:791-793, 1986.
Fukushima and Hatfield, *J. Agric. Food Chem.* 52:3713-3720, 2004.
Gallie et al., *The Plant Cell*, 1:301-311, 1989.
Gelvin et al., *In: Plant Molecular Biology Manual*, 1990.
Ghosh-Biswas et al., *J. Biotechnol.*, 32(1):1-10, 1994.
Goering et al., *Forage Fiber Analysis*, Vol. 379. U.S. Government Printing Office, Washington, D.C. 1970.
Gong et al. *Adv. Biochem. Engng. Biotech.* 65: 207-241, 1999.
Grabber et al., *Crop Sci* 32: 806-810), 1992.
Grabber, et al., *J Agric Food Chem* 45:2530-2532, 1997.
Guo et al., *Plant Cell* 13:73-88 (2000).
Guo et al., *Transgenic Res.* 10:457-464 (2001).
Haemelinck et al., *Biomass and Bioenergy* 28:84, 2005.
Hagio et al., *Plant Cell Rep.*, 10(5):260-264, 1991.
Hamilton et al., *Proc. Natl. Acad. Sci. USA*, 93(18):9975-9979, 1996.
Hansen et al., *Chem. Phys. Lipids.*, 108:135-150, 2000.
Haseloff et al., *Proc. Natl. Acad. Sci. USA*, 94(6):2122-2127, 1997.
He et al., *Plant Cell Reports*, 14 (2-3):192-196, 1994.
Hensgens et al., *Plant Mol. Biol.*, 22(6):1101-1127, 1993.
Hiei et al., *Plant. Mol. Biol.*, 35(1-2):205-218, 1997.
Hillard et al., *J. Neurochem.*, 64:677-683, 1995.
Hinchee et al., *Bio/technol.*, 6:915-922, 1988.
Hoffmann et al., Plant Cell 16:1446-1465, 2004.
Hou and Lin, *Plant Physiology*, 111:166, 1996.
Hu et al., *Nat. Biotechnol.* 17:808-812 (1999)
Hudspeth and Grula, *Plant Mol. Biol.*, 12:579-589, 1989.
Ikuta et al., *Bio/technol.*, 8:241-242, 1990.
Ishidia et al., *Nat. Biotechnol.*, 14(6):745-750, 1996.
Jung and Vogel, *J Anim Sci* 62:1703-1712, 1986
Kaeppler et al., *Plant Cell Reports* 9: 415-418, 1990.
Kaeppler et al., *Theor. Appl. Genet.*, 84(5-6):560-566, 1992.
Katz et al., *J. Gen. Microbiol.*, 129:2703-2714, 1983.
Khanolkar et al., *Chemistry and Physics of Lipid* 108:37-52, 2000.
Klee et al., *Bio-Technology*, 3(7):637-642, 1985.
Knittel et al., *Plant Cell Reports*, 14(2-3):81-86, 1994.
Krogh et al., *J. Mol. Biol.*, 305:567-580, 2001.
Lambert and Di Marzo, *Current Med. Chem.*, 6:663-674, 1999.
Lambert et al., *Current Med. Chem.*, 9:739-755, 2002.
Lapierre et al., *J. Wood Chem. Technol.* 5:277-292 1985.
Lapierre et al., *Res. Chem. Intermed.* 21: 397-412, 1995.
Lawton et al., *Plant Mol. Biol.* 9:315-324, 1987.
Lazzeri, *Methods Mol. Biol.*, 49:95-106, 1995.
Lee et al., *Adv. Biochem. Engng. Biotech.*, 65: 93-115, 1999
Lee et al., *Korean J. Genet.*, 11(2):65-72, 1989.
Lehner et al., *Brief Funct Genomic Proteomic*, April; 3(1): 68-83, 2004.
Lewis, *Current Opinion in Plant Biology* 2:153-162, 1999.
Lorz et al., *Mol Gen Genet*, 199:178-182, 1985.
Marcotte et al., *Nature*, 335:454, 1988.
McCabe, Martinell, *Bio-Technology*, 11(5):596-598, 1993.
McCormac et al., *Euphytica*, v. 99 (1) p. 17-25, 1998.
McLaughlin, S. B. and M. E. Walsh. *Biomass Bioenergy* 14:317-324, 1998.
Mes-Hartree, et al. *Appl. Microbiol. Biotechnol.*, 29:462-468, 1988.
Morjanoff and Gray, *Biotechnol. Bioeng.* 29:733-741, 1987.
Murakami et al., *Mol. Gen. Genet.*, 205:42-50, 1986.
Murashige and Skoog, *Physiol. Plant.*, 15:473-497, 1962.
Nagatani et al., *Biotech. Tech.*, 11(7):471-473, 1997.
Odell et al., *Nature*, 313:810-812, 1985.
Ogawa et al., *Sci. Rep.*, 13:42-48, 1973.
Olsson and Hahn-Hagerdal, *Enzyme and Microb. Technol.* 18:312-331, 1996.
Omirulleh et al., *Plant Mol. Biol.*, 21(3):415-428, 1993.
Ow et al., *Science*, 234:856-859, 1986.

Paria and Dey, *Chem. Phys. Lipids,* 108:211-220, 2000.
PCT App. WO 94/09699
PCT App. WO 95/06128
PCT App. WO 97/41228
PCT App. WO 97/4103
PCT App. WO 92/17598
PCT App. WO 2006/012594
Pertwee et al., *Eur. J. Pharmacol.,* 272:73-78, 1995.
Pertwee, *Prog. Neurobiol.,* 63:569-611, 2001.
Pilat, *Nature Biotechnology,* 20:607, 2002.
Potrykus et al., *Mol. Gen. Genet.,* 199:183-188, 1985.
Prasher et al., *Biochem. Biophys. Res. Commun.,* 126(3): 1259-1268, 1985.
Reddy et al., *Proc. Nat. Acad. Sci. U.S.A.,* 102:16573-16578, 2005.
Reggio P H, *Tocris Reviews* 10:1-5, 1999.
Reichel et al., *Proc. Natl. Acad. Sci. USA,* 93: 5888-5893. 1996.
Reynolds, *Nat. Biotechnol.* 22: 326-330, 2004.
Rhodes et al., *Methods Mol. Biol.,* 55:121-131, 1995.
Richards et al., *Plant Cell Rep.* 20:48-54, 2001.
Ritala et al., *Plant Mol. Biol.,* 24(2):317-325, 1994.
Rogers et al., *Methods Enzymol.,* 153:253-277, 1987.
Sambrook et al., In: *Molecular Cloning-A Laboratory Manual* (second edition), Cold Spring Harbour Laboratory Press, 1989.
Sarker et al., *FEBS Lett.,* 472:39-44, 2000.
Schmid and Berdyshev, *Prostag. Leukotr. Essent. Fatty Acids,* 66:363-376, 2002.
Schmid et al., *Chem. Phys. Lipids,* 121:111-134, 2002.
Schmid et al., *Prog. Lipid Res.,* 29:1-43, 1990.
Sederoff, et al, *Current Opinion in Plant Biology* 2:145-152, 1999.
Shadle, et al., "Effects Of Down-Regulation Of HCT On Lignin In Alfalfa." Phytochemical Society of North America Annual Meeting, Jul. 8-12, 2006, Oxford, Miss.
Sheen et al., *Plant Journal,* 8(5):777-784, 1995.
Shrestha et al., *J. Biol. Chem.* 278: 34990-34997, 2003.
Shrestha et al., *Plant Physiol.,* 130:391-401, 2002.
Singsit et al., *Transgenic Res.,* 6(2):169-176, 1997.
Somleva et al. *Crop Science,* 42:2080-2087, 2002.
Stalker et al., *Science,* 242:419-422, 1988.
Sticklen, *Curr. Op. Biotechnol.* 17:315-319, 2006.
Straus S E, Proc Natl Acad Sci USA 97: 9363-9364, 2000.
Sullivan et al., *Mol. Gen. Genet.,* 215(3):431-440, 1989.
Sun and Cheng, *Bioresource Technol.* 83:1-11, 2002.
Sutcliffe, *Proc. Natl. Acad. Sci. USA,* 75:3737-3741, 1978.
Tabe, et al., *Genetica,* 90:181-200, 1993.
Thillet et al., *J. Biol. Chem.,* 263:12500-12508, 1988.
Thomas et al., *Plant Sci.* 69:189-198, 1990.
Thompson et al., *Euphytica,* 85(1-3):75-80, 1995.
Thompson et al., *The EMBO Journal,* 6(9):2519-2523, 1987.
Tian, Sequin, Charest, *Plant Cell Rep.,* 16:267-271, 1997.
Tingay et al., *The Plant Journal* v. 11 (6) p. 1369-1376. 1997.
Tomes et al., *Plant. Mol. Biol.* 14(2):261-268, 1990.
Torbet, Rines, Somers, *Crop Science,* 38(1):226-231, 1998.
Torbet, Rines, Somers, *Plant Cell Reports,* 14(10):635-640, 1995.
Toriyama et al., *TheorAppl. Genet.,* 73:16, 1986.
Triparthy et al., *Plant Physiol* 131: 1781-1791, 2003a
Tripathy et al., In *Advanced Research on Plant Lipids,* 2002: 315-318, N. Murata et al., (eds), 2003b
Tripathy et al., *Plant Physiol.,* 121:1299-1308, 1999.
Tsukada; Kusano; Kitagawa, *Plant Cell Physiol.,* 30(4)599-604, 1989.
Tusnády and Simon, *J. Mol. Biol.* 283, 489-506, 1998.
Tusnády and Simon, *Bioinformatics* 17, 849-850, 2001.
Twell et al., *Plant Physiol* 91:1270-1274, 1989.
Uchimiya et al., *Mol. Gen. Genet.,* 204:204, 1986.
Van der Stelt et al., *J. Neurosci,* 21:765-8771, 2001.
Van Eck; Blowers; Earle, *Plant Cell Reports,* 14(5):299-304, 1995.
Vasil et al., *Plant Physiol.,* 91:1575-1579, 1989.
Vogel et al., Crop Sci. 39:276-279 (1999)
Vogel and Jung, ORNL/Sub/90-90OR21954/1, 2000.
Walker et al., *Proc. Natl. Acad. Sci. USA,* 84:6624-6628, 1987.
Wang et al., *Molecular and Cellular Biology,* 12(8):3399-3406, 1992.
Whetten and Sederoff, *Forest Ecology and Management* 43:301-316, 1991.
Wilson and Nicoll, *Science,* 296:678-682, 2002.
Wyman, *Annu. Rev. Energy Environ.* 24:189-226, 1999.
Yamada et al., *Plant Cell Rep.,* 4:85, 1986.
Yang and Russell, *Proc. Natl. Acad. Sci. USA,* 87:4144-4148, 1990.
Zhang et al., "Science 267:240-243, 1995.
Zheng and Edwards, *J. Gen. Virol.,* 71:1865-1868, 1990.
Zhou et al., *Plant Cell Reports,* 12(11). 612-616, 1993.
Zukowsky et al., *Proc. Natl. Acad. Sci. USA,* 80:1101-1105, 1983.

What is claimed is:

1. A transgenic switchgrass plant comprising a selected DNA that down regulates caffeic acid O-methyltransferase (COMT) through inhibition or translation of a COMT gene and reduces lignin biosynthesis in the plant and wherein the plant exhibits an increase in fermentable carbohydrates relative to a plant of the same genotype lacking the selected DNA, wherein the inhibition of transcription or translation is accomplished by expression of a nucleic acid from said selected DNA complementary to all or part of the COMT gene; wherein the selected DNA comprises SEQ ID NO: 5 or a fragment of at least 100 contiguous nucleotides thereof, or a sequence with at least 95% identity to SEQ ID NO: 5.

2. The transgenic plant of claim 1, further comprising a second selected DNA that down regulates a lignin biosynthesis gene selected from the group consisting of 4-coumarate 3-hydroxylase (C3H), phenylalanine ammonia-lyase (PAL), cinnamate 4-hydroxylase (C4H), hydroxycinnamoyl transferase (HCT), caffeoyl CoA 3-O-methyltransferase (CCoAOMT), cinnamyl alcohol dehydrogenase (CAD), cinnamoyl CoA-reductase (CCR), 4-coumarate-CoA ligase (4CL), monolignol-lignin-specific glycosyltransferase, and aldehyde dehydrogenase (ALDH), wherein down regulation of said lignin biosynthesis gene is accomplished by expression of nucleic acid sequence complementary to all or part of the lignin biosynthesis gene.

3. The transgenic plant of claim 1, wherein the selected DNA is an antisense or RNAi construct.

4. The transgenic plant of claim 3, wherein the antisense of RNAi construct comprises a promoter selected from the group consisting of a developmentally-regulated, organelle-specific, inducible, tissue-specific, constitutive, cell-specific, seed specific, and germination-specific promoter.

5. The transgenic plant with the selected DNA, further defined as an R0 transgenic plant.

6. The transgenic plant of claim 1, further defined as a progeny plant of any generation of an R0 transgenic plant with the selected DNA, wherein the transgenic plant has inherited the selected DNA from the R0 transgenic plant.

7. The transgenic plant of claim 1, wherein at least two lignin biosynthesis genes are down-regulated.

8. The transgenic plant of claim 7, wherein at least three lignin biosynthesis genes are down-regulated.

9. The transgenic plant of claim 8, wherein at least four lignin biosynthesis genes are down-regulated.

10. A seed of the transgenic plant of claim 1, wherein the seed comprises the selected DNA.

11. A transgenic cell of the transgenic plant of claim 1.

12. A method of increasing the level of one or more fermentable carbohydrates in a switchgrass plant comprising down-regulating a caffeic acid O-methyltransferase (COMT) in the plant through inhibition of transcription or translation of a COMT gene, wherein the inhibition of transcription or translation is accomplished by introducing and expressing a nucleic acid sequence from a selected DNA complementary to all or part of the COMT gene; wherein the selected DNA comprises SEQ ID NO: 5 or a fragment thereof of at least 100 contiguous nucleotides thereof, or a sequence with at least 95% identity to SEQ ID NO: 5.

13. The method of claim 12, wherein the nucleic acid sequence is in the antisense orientation.

14. The method of claim 12, wherein the fermentable carbohydrate is selected from the group consisting of xylose, arabinose, mannose, glucose, galactose, xyloglucan, arabinoglucan, galacturonan, starch, and cellobiose.

15. The method of claim 12, wherein the nucleic acid sequence is an antisense or RNAi construct.

16. The method of claim 12, further comprising down-regulating at least a first enzyme activity selected from the group consisting of: 4-coumarate 3-hydroxylase (C3H), phenylalanine ammonia-lyase (PAL), cinnamate 4-hydroxylase (C4H), hydroxycinnamoyl transferase (HCT), caffeoyl coA 3-O-methyltransferase (CCoAOMT), cinnamyl alcohol dehydrogenase (CAD), cinnamoyl CoA-reductase (CCR), 4-coumarate-CoA ligase (4CL), monolignol-lignin-specific glycosyltransferase, and aldehyde dehydrogenase (ALDH).

17. The method of claim 16, wherein the down-regulating comprises introducing into the plant a second selected DNA that down-regulates 3-hydroxylase (C3H) and/or hydroxycinnamoyl transferse (HCT).

18. The method of claim 12, wherein introducing the nucleic acid sequence comprises plant breeding.

19. The method of claim 12, wherein introducing the nucleic acid sequence comprises genetic transformation.

20. A method for the producing lignocellulosic biomass, comprising:
(a) obtaining the plant according to claim 1; and
(b) harvesting the lignocellulosic biomass from the plant.

21. A method for producing ethanol comprising:
(a) obtaining lignocellulosic biomass from the switchgrass plant according to claim 1,
(b) treating the biomass to render carbohydrates in the biomass fermentable and wherein at least about 40% of the total carbohydrates present in the biomass are released and fermentable; and
(c) fermenting the carbohydrates to produce ethanol.

22. The method of claim 21, wherein the step of treating the biomass comprises contacting the biomass with a cellulolytic enzyme.

23. The method of claim 22, wherein the biomass is contacted with the cellulolytic enzyme without an acid pretreatment step.

24. The method of claim 22, further comprising pretreating the biomass with an acid prior to contacting the biomass with the cellulolytic enzyme.

25. The method of claim 21, wherein the plant further comprises a second selected DNA that down regulates an enzyme selected from the group consisting of: 4-coumarate 3-hydroxylase (C3H), phenylalanine ammonia-lyase (PAL), cinnamate 4-hydroxylase (C4H), hydroxycinnamoyl transferase (HCT), caffeoyl coA 3-O-methyltransferase (CCoAOMT), cinnamyl alcohol dehydrogenase (CAD), cinnamoyl CoA-reductase (CCR), 4-coumarate-CoA ligase (4CL), monolignol-lignin-specific glycosyltransferase, and aldehyde dehydrogenase (ALDH).

* * * * *

SEQUENCE LISTING

```
<160> NUMBER OF SEQ ID NOS: 10

<210> SEQ ID NO 1
<211> LENGTH: 1539
<212> TYPE: DNA
<213> ORGANISM: Cynodon dactylon

<400> SEQUENCE: 1
atggacgtct ccctcatcct ctctgtgtcc atcgcgctgg tggcgatccc gctctcgctg      60
gcgctgctga accggctccg cctcgggcgc ctgccgccgg gcccgcggcc ctggcccgtg     120
gtgggcaacc tccgccagat caagcccgtg cggtgccgct gcttccagga gtgggcggag     180
cggtacggcc ccatcatctc cgtctggttc gggtccgggc tcacggtggt cgtgtccacc     240
tccgagctcg cgcgggaggt gctcaaggag aacgaccagc agctcgccga ccggccgcgg     300
aaccgctcca cgcagcggtt cagccgcaac ggccaggacc tgatctgggc cgactacggc     360
```

```
ccgcactaca tcaaggtgcg caagctctgc aacctcgagc tcttcacgcc caagcgactc     420
gaggcgctgc gccccatccg cgaggacgag atcaccgcca tggtcgagtc cgtccaccgc     480
gccgccaccg ccgccggtaa tgaaggaaaa ccaatggttg tgaggaacca cctttctatg     540
gtggccttca acaatattac aaggcttgca tttgggaagc ggttcatgaa tgcgaatggt     600
gagattgatg aacaggggcg tgagttcaag accattgtca acaacgggat taagatcggt     660
gcatctctct ctgttgctga gtttatttgg tatttgaggt ggttgtgtcc gcttaacgag     720
gagctataca aacccacaa tgagagaagg atcgcctaa ccaagaaaat cattgatgag       780
catgccaaag ctctcaagga gagtggtgct aagcagcact tgttgatgc attgttcacc      840 ctcagggatc aatacaatct tagcgacgac acagttattg gacttctatg ggacatgatc     900
actgctggaa tggacaccac agtgatttca gtagaatggg caatggcgga gctagtcagg     960
aacctcaggg tgcagaagaa gttgcaggag gaactggacc gtgttgttgg ccacgaccgt    1020
gtcatgtctg agactgattt ccagaacctc ccctaccttc aagccgtagt caaagagtcc    1080
ctacggctgc acccgccgac accactcatg ctccctcaca aggcaagcac aagtgtcaag    1140 atcgcggct acaacatccc caaggggcc aacgtgatgg tgaatgtctg ggcagtggca      1200
cgtgatccca aggtgtggaa caacccactg gagttcaggc cggagcgctt cctggaggag    1260
aacattgata tcaagggtag cgacttcagg gttcttcctt tcggagctgg ccggcgagtg    1320
tgccccggtg cgcaacttgg catcaacctc gtagcctcca tgatcgggca cctgctgcac    1380
cacttcgagt ggtcactgcc ggagggcacc aagccggagg acgtcaacat gatggaatcc    1440
gccggactcg tcacgttcat gggaaagccg ctgcaagctg tagccaagcc gcgcctgaag    1500
aaggaggagc tgtacaagag ggtcccggtt gagatgtga                           1539

<210> SEQ ID NO 2
<211> LENGTH: 789
<212> TYPE: DNA
<213> ORGANISM: Cynodon dactylon

<400> SEQUENCE: 2
atggcgtcca cggcaaccga ggcggcggcg cagcctgcgg cggcggagca gcagcaggtc      60
aacggcaacg gcgagcagaa gacgcgccac tccgaggtcg ggcacaagag cctgctcaag     120
agcgacgacc tctaccagta catcctggag acgagcgtgt acccgcggga gccggagagc     180
atgaaggagc tccgtgaggt caccgccaag cacccgtgga acctgatgac gacgtcggcg     240
gacgagggcc agttcctcaa catgctgctc aagctcatcg gcgccaagaa gaccatggag     300
atcggcgtct acaccggcta ctcccctcctc gccaccgcgc tcgccatccc gaggacggc      360 acgatcttgg ccatggacat caaccgcgag aactacgagc tcggcctgcc ctgcatcgag     420
aaggccggcg tcgcccacaa gatcgacttc cgcgagggac cggcgctccc cctcctcgac     480
cagctcctgg aagacgaggc caaccacggc tcgttcgact tcgtcttcgt cgacgccgac     540
aaggacaact acctcaacta ccacgagcgg ctgatgaagc tcgtgaagac gggcggcctc     600
gtcggctacg acaacacgct ctggaacggc tccgtcgtgc tccccgccga cgcgcccatg     660
cgcaagtaca tccgctacta ccgcgacttc gtgctcgagc tcaacaaggc gctcgccgcc     720
gacgagcgcg tcgagatctg ccagctcccc gtcggagacg gcatcaccct ctgccgccgc     780
gtcaagtga                                                             789

<210> SEQ ID NO 3
```

```
<211> LENGTH: 250
<212> TYPE: DNA
<213> ORGANISM: Panicum virgatum

<400> SEQUENCE: 3
tctcccacat ggacgttgac accgtggcgt tcacggggtc cacggaggtc ggccgcctca    60
tcatggagtc ggccgcgagg agcaacctca agccggtctc tctggagctc ggcggcaagt   120
cgccgctcat catcttcgac gacgccgacg tcgacatggc cgtcaacctg tcgcggctcg   180
ccatcttctt caacaagggg gagatctgcg cggccggatc gcgcgtctat gtgcaggaag   240
ggatctacga                                                          250

<210> SEQ ID NO 4
<211> LENGTH: 600
<212> TYPE: DNA
<213> ORGANISM: Panicum virgatum

<400> SEQUENCE: 4
gaagatgtgg tggtcaaggt gctgtactgt gggatttgcc atactgacat ccaccaggcc    60
aagaaccacc tcggcgcttc caagtacccc atggtccctg gcatgaggt ggtcggcgag   120
gtggtggagg tcgggcccga ggtgagcaag caccgcgtcg cgacgtcgt tggcgtcggg   180
gtgatcgtcg ggtgctgccg cgagtgccgc ccctgcaagg ccaacgtcga gcagtactgc   240
aacaaggaga tctggtccta caacgacgtc tacaccgacg ccaacccac gcagggcggg   300
ttcgcctcca ccatggtcgt cgacccgaag ttcgtggtgc cgatcccggc aggcctggcg   360
ccggagcagg cggcgccgct gctgtgcgcg gtgtgacggt tgtacagccc gctgaagcac   420
ttcgggctga cggccccggg cctccgcggc ggcatcctgg ggctcggcgg cgtgggccac   480
atgggcgtga aggtggcgaa ggcgatgggc caccacgtga cggtgatcag ctcgtcgtcc   540
cggaagcgcg cggaggcgat ggacgagctg gcgcggacg cgtacctggt gagctccgac   600

<210> SEQ ID NO 5
<211> LENGTH: 558
<212> TYPE: DNA
<213> ORGANISM: Panicum virgatum
<220> FEATURE:
<221> NAME/KEY: misc_feature
<222> LOCATION: (381)..(381)
<223> OTHER INFORMATION: n is a, c, g, or t
<220> FEATURE:
<221> NAME/KEY: misc_feature
<222> LOCATION: (419)..(420)
<223> OTHER INFORMATION: n is a, c, g, or t

<400> SEQUENCE: 5
aggtcctcat ggagagctgg tactacctca aggacgcggt gctggagggc ggcatcccgt    60
tcaacaaggc gtacggcatg acggcgttcg agtaccacgg cacggacccg cgcttcaacc   120
gcgtgttcaa cgagggcatg aagaaccact cggtgatcat caccaagaag ctgctcgagt   180
ctacgccgg cttcgagggc gtcggcaccc tggtcgacgt cggcggcggc gtcggcgcca   240
ccctgcacgc catcacctcc cgctaccccg gcatcagggg ggtcaacttc gacctgcccc   300
acgtgatctc cgaggcgccg ccgttccccg gcgtggagca cgtcggcggg gacatgttca   360
aggccgtgcc cgccggcgac nccatcctca tgaagtggat cctccacgac tggagcgann   420
cccactgcgc ggcgatcctc aagaactgct acgacgcgct ccccgccggc ggcagggtga   480
tcgccgtcga gtgcatcctg ccggcgaacc cggaggcgac gcccaaggcg cagggcgtct   540
tccacgtcga catgatca                                                 558
```

<210> SEQ ID NO 6
<211> LENGTH: 1518
<212> TYPE: DNA
<213> ORGANISM: Festuca arundinacea
<220> FEATURE:
<221> NAME/KEY: misc_feature
<222> LOCATION: (661)..(661)
<223> OTHER INFORMATION: n is a, c, g, or t

<400> SEQUENCE: 6

| | | | | | |
|---|---|---|---|---|---|
| atggatttcg | tgttcgtgga | gaagctcctc | gtcggccttc | ttgcgtccgt | ggtggtcgcg | 60 |
| atcgtggtgt | ccatgatccg | cggccgcaaa | ctgaggctgc | cgcctggccc | catccccgtg | 120 |
| cccatcttcg | gcaactggct | gcaggtcggg | gacgacctca | accaccgcaa | cctggcggcg | 180 |
| atggcccgca | agttcggcga | ggtcttcctc | tccgcatgg | gcatccgcaa | ccttgtggtg | 240 |
| gtgtccagcc | cggagctggc | caaggaggtg | ctccacacgc | agggcgtgga | gttcgggtcc | 300 |
| cggacccgga | acgtggtgtt | cgacatcttc | acgggcaagg | gcaggacat | ggtgttcacc | 360 |
| gtgtacggcg | accactggcg | caagatgcgg | cggatcatga | cggtgcccct | cttcacgaac | 420 |
| aaggtggtgc | agcagtaccg | ggccgggtgg | gaggcggagg | ggcctttcgt | ggtggacaac | 480 |
| gtgcgcgccg | accccagggc | cgccaccgac | ggcgtggtgc | tccgccgcca | cctgcagctg | 540 |
| atgatgtaca | caacatgta | ccgcatcatg | ttcgaccggc | ggttcgagag | catggacgac | 600 |
| ccgctcttcc | tccgcctcag | ggagctcaac | ggcgagcgca | gccgcctcgc | gcagagcttc | 660 |
| nagtacaact | acggcgactt | catccccgtc | ctccgcccct | tcctccgcgg | ctacctcagg | 720 |
| ctgtgcgagc | aggtcaagga | gacccgcctc | aagctgttca | aggattactt | cctggacgag | 780 |
| aggaagaagc | tggcaagcac | caagcccatg | gacaacaacg | gcctcaagtg | cgccattgat | 840 |
| cacatcctgg | aggcgcagca | gaaggggggag | atcaacgagg | acaacgtcct | ctacatcatc | 900 |
| gagaacatca | cgtcgccgc | gatcgagacg | acgttgtggt | cgatcgagtg | ggggatcgcg | 960 |
| gagctggtga | accacccgga | gatccagcag | aagctgcggg | acgagatgga | cgcggtgctg | 1020 |
| ggcgccggcc | accagatcac | ggagtccgac | acgcacaggc | tccccctacct | gcaggcggtg | 1080 |
| atcaaggaga | cgctgcggct | gcgcatggcc | atcccgctgc | tggtgccgca | catgaacctc | 1140 |
| cacgatgcca | agctcgccgg | ctacaacatc | cccgccgaga | gcaagatcct | cgtcaacgcc | 1200 |
| tggttcctcg | ccaacaaccc | ggagcagtgg | aagcggcccg | acgagttccg | ccggagcgc | 1260 |
| ttcctggagg | aggagaggca | cgtggaggcc | agcggcaacg | acttcaggtt | cctgcccttc | 1320 |
| ggcgtcggcc | gccggagctg | cccgggggatc | atcctcgcgc | tgcccatcct | cggcatcacc | 1380 |
| atcggccgcc | tcgtgcagaa | cttcgagctc | accacgccgc | ccggggtgga | caagctcgac | 1440 |
| accaccgaga | agggcggcca | gttcagcctc | cacatcttga | accactccac | catcgtcgcc | 1500 |
| aagcccagag | tgttctga | | | | 1518 |

<210> SEQ ID NO 7
<211> LENGTH: 1086
<212> TYPE: DNA
<213> ORGANISM: Festuca arundinacea

<400> SEQUENCE: 7

| | | | | | |
|---|---|---|---|---|---|
| atgggcagcg | tcgacgcctc | cgagaagacg | atcaccgggt | gggccgccag | ggacgccacc | 60 |
| ggccacctct | cccctacac | gtacaacctc | aggaggacgg | cgctgaaga | tgtggtgctg | 120 |
| aaggttctgt | actgcggcat | ctgccacact | gacctccacc | agaccaagaa | ccaccttggt | 180 |

```
gcttcaaaat accccatggt acccgggcat gaggtggtag gcgaggtggt ggaggtcggg      240
ccggaggtga gcaagtacag cgtcggcgac gtggtcggcg tgggggtgat cgtcgggtgc      300
tgccgcgact gccggccgtg caaggccaac gttgagcagt actgcaacaa gaagatctgg      360
tcgtacaacg acgtctacac cgacggcaag cccacgcagg gcggcttcgc ctcctccatg      420
gtcgtcgacc agaagttcgt ggtgaagatc ccagcggggc tagcgccgga gcaggcggcg      480
ccgctgctgt gcgccggcgt gaccgtgtac agcccgctga agcacttcgg gctgatgacc      540
ccgggcctcc gcggcggcat cctcggcctc ggcggcgtcg gccacatggg cgtgaaggtg      600
gccaagtcca tgggccacca cgtcaccgtg atcagctcct ccgacaagaa gcgcgccgag      660
gccatggacg acctgggcgc cgacgcctac ctcgtcagct ccgacgaggc ccagatggcc      720
gccgccatgg actcgctgga ctacatcatc gacaccgtgc ccgtcaagca cccgctcgag      780
ccctacctcg cgctcctcaa gatggacggc aagctcgtcc tcatgggcgt catcggcgag      840
ccgctcagct tcgtgtcccc catggtcatg ctcggaagga agaccatcac cggcagcttc      900
atcgggagca tcgaggagac cgaggaggtg cttaggttct gcgtcgaaaa gggcctcacc      960
tcgcagatcg aggtcgtcaa gatggactac ctcaaccagg cgctcgagag gctcgagcgc     1020
aacgacgtca ggtaccgctt cgtcgtcgac gtcgcaggga gcaacatcga cgacactgcc     1080
gcgtga                                                                 1086

<210> SEQ ID NO 8
<211> LENGTH: 801
<212> TYPE: DNA
<213> ORGANISM: Festuca arundinacea

<400> SEQUENCE: 8
atggcgacca cggcggctga tgccacggcc acggtggcaa aggagcagca gaccaccacc       60
aacggcgccg ccagcgctgg cgagcaggtc acgcgccact ccgaggtcgg acacaagagc      120
ctgctccaga gcgacgcgct ctaccagtac atcctggaga ccaccgtgta cccgcgcgag      180
cacgagtgca tgaagcagct ccgccaggac accgcgaacc acccctggaa cctgatgacc      240
acgtcggcgg acgagggcca gttcctgaac ctgctcatca gctcatcgg cgccaagaag      300 accatggaga tcggcgtcta caccggctac tccctcctcg ccaccgcact cgccatcccc      360
gaagacggaa ccatcttggc catggacatc aaccgcgaga actacgagac catcggcaag      420
ccctgcatcg agaaggccgg cgtcgcgcac aagatcgact ccgcgagggg cccggccctc      480
ccggtcctgg acgagctgct ccaggacgag gccaaccacg gcaccttcga cttcgtcttc      540
gtcgacgccg acaaggacaa ctacctcaac taccacgagc gcctcatgaa gctcgtcagg      600
gtcggcggac tcctcggcta ctacaacacg ctctggaacg gatccgtcgt gctccccgcc      660
gacgcgccca tgcgcaagta catccgctac taccgcgact tcgtcctcga gcttaacaag      720
gccctcgccg cagacgaccg cgtcgagatc tgccagctcc ccgtcggcga cggcatcaca      780
ctctgccgcc gcgccaagtg a                                                801

<210> SEQ ID NO 9
<211> LENGTH: 1083
<212> TYPE: DNA
<213> ORGANISM: Festuca arundinacea

<400> SEQUENCE: 9
atgggttcca ccgccgccga catggccgcg tccgccgacg aggaggcgtg catgttcgcc       60
ctccagctcg cctcctcgtc gatcctcccg atgacgctga agaacgccat cgagcttggc      120
```

```
ctcctggaga tcctggtggc cgccggcggc aagtcgctga ccccaccga ggtggccgcc    180 aagctcccgt ccgcggcgaa cccggaagcg ccggacatgg tggaccgcat gctccggctg    240
ctcgcgtcgt acaacgtcgt gacgtgcctg gtagaggagg gcaaggacgg gcgcctctcc    300
cggagctacg gcgccgcgcc cgtgtgcaag ttcctcaccc caacgagga cggcgtctcc    360 atggcggcgc tcgcgctcat gaaccaggac aaggtcctca tggagagctg gtactacctc    420
aaggacgcgg tccttgacgg cggcatcccc ttcaacaagg cgtacggcat gtcggcgttc    480
gagtaccacg gcacggaccc gcgcttcaac cgcgttttca acgaagggat gaagaaccac    540
tccatcatca tcaccaagaa gctcctcgag ctctaccacg gcttccaggg cctcggcacc    600
ctcgtcgacg tcggcggcgg cgtcggcgcc accgtggccg ccatcgccgc ccactacccc    660
gccatcaagg gggtcaactt cgacctcccc cacgtcatct ccgaggcgcc gcagttcccg    720
ggcgtcaccc acgtcggcgg cgacatgttc aaggaggtgc cctcgggcga cgccatcctc    780
atgaagtgga tcctccacga ctggagcgac cagcactgcg ccacgctgct caagaactgc    840
tacgacgcgc tgccggcgca cggcaaggtc gtgctcgtcg agtgcatcct gccggtcaac    900
ccggaggcca agcccagctc gcaggggggtc ttccacgtcg acatgatcat gctcgcgcac    960
aaccccggcg gcagggagag gtacgagagg gagttcgagg ccctggccag gggagctggg   1020
ttcaccggcg tcaagtccac gtacatctac gcaaacgcgt gggccatcga gttcaccaag   1080
tag                                                                1083

<210> SEQ ID NO 10
<211> LENGTH: 730
<212> TYPE: DNA
<213> ORGANISM: Panicum virgatum

<400> SEQUENCE: 10
aagagctgct gctaccacca atccggtcgc cggattcgtc cggagctttg cccgtttcgc      60
ggacccagat ctactccgcg gcgccggcgc gtccccgctg agatggcgat cacggtgagg     120
cggtcaacga tggtgtaccc tgcgcgggag acgccgcggc aacggctgtg gaactccaac     180
ctcgacctcg tggtgccgcg cttccacacg cccagcgtct acttctaccg ccgcggcggc     240
cccgaggtgg aggggttctt cgacagcgag cggatgcggc gcgcgctggc ggaggcgctc     300
gtgccgttct acccgatggc ggggcgcctc gcgcgggacg aggacggcag ggtcgagatc     360
gactgcaacg gcgaaggggt gctcttcgtc gaggccgacg cgcccaacgc cgccgtcgac     420
aactacggcg atttcgcgcc caccatggag ctcaagcgcc taatcccggc ggtcgattac     480
accgatgaca tctcggcctt cccgctcctc gtgctccagg tgacttactt caaatgtgga     540
ggcgtctccc ttggtgttgg catgcaacac catgtagcgg atggcatgtc cggcttgcac     600
ttcattaact catggtctga cctctgccgt ggagctcaaa tttctgtcat gcccttcatt     660
gaccgcactc tccttcgcgc tcatgatcca ccgactccat ctttccaaca tattgagtac     720
cagcctgccc                                                           730
```